US012631609B2

(12) United States Patent
Yamada et al.

(10) Patent No.: US 12,631,609 B2
(45) Date of Patent: May 19, 2026

(54) MEASUREMENT SYSTEM, MEASUREMENT METHOD, AND COMPUTER PROGRAM

(71) Applicant: Hitachi, Ltd., Tokyo (JP)

(72) Inventors: Masuyoshi Yamada, Tokyo (JP);
Yasutaka Serizawa, Tokyo (JP);
Hisanori Matsumoto, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 447 days.

(21) Appl. No.: 18/370,079

(22) Filed: Sep. 19, 2023

(65) Prior Publication Data

US 2024/0255480 A1 Aug. 1, 2024

(30) Foreign Application Priority Data

Jan. 30, 2023 (JP) ................................. 2023-012218

(51) Int. Cl.
*G01N 33/00* (2006.01)

(52) U.S. Cl.
CPC ................................. *G01N 33/0008* (2013.01)

(58) Field of Classification Search
CPC ............. G01N 33/0006; G01N 21/274; G01N 33/007; G01N 2021/7773; G01N 2021/7783; G01N 2021/7786; G01N 21/27; G01N 21/3504; G01N 21/6456; G01N 21/77; G01N 21/78; G01N 21/80; G01N 2201/0221; G01N 2201/1211; G01N 2201/127; G01N 2201/12723; G01N 2201/12753; G01N 2201/12792; G01N 27/4146; G01N 27/4163; G01N 33/0008; G01N 33/0009; G01N 33/0031;

G01N 33/0034; G01N 33/004; G01N 33/0062; G01N 33/0068; G01N 33/0072; G01N 33/0073; G01N 33/0075; G01N 33/02; G01N 33/025
See application file for complete search history.

(56) References Cited

U.S. PATENT DOCUMENTS

| | | | | |
|---|---|---|---|---|
| 6,418,783 B2 * | 7/2002 | Sunshine | ........... | G01N 33/0009 |
| | | | | 702/119 |
| 11,263,498 B2 * | 3/2022 | Kim | ...................... | G06T 7/0002 |
| 11,899,001 B2 * | 2/2024 | Makaram | ........... | G01N 33/0073 |
| 2008/0312859 A1 | 12/2008 | Skyggebjerg et al. | | |

(Continued)

FOREIGN PATENT DOCUMENTS

JP 2008-511373 A 4/2008

*Primary Examiner* — Mohammad K Islam
(74) *Attorney, Agent, or Firm* — Miles & Stockbridge, P.C.

(57) ABSTRACT

An easy-to-maintain measurement system including a first sensor that measures a target and outputs a predetermined physical quantity, a second sensor that measures the target and outputs the same type as the predetermined physical quantity, and a processor configured to (1) acquire a first value from the first sensor and a second value from the second sensor, (2) convert the first value to the value of the physical quantity by a first calibration data, (3) calculate second calibration data for the second sensor from the second value and the predetermined physical quantity obtained in step (2), (4) convert the second value to the physical quantity by the second calibration data, and (5) detect the state of the measurement target by an estimation model and the physical quantity obtained in step (4).

13 Claims, 13 Drawing Sheets

(56)  References Cited

U.S. PATENT DOCUMENTS

| | | | | |
|---|---|---|---|---|
| 2013/0074575 A1* | 3/2013 | Duric | ................. | G01N 33/0006 |
| | | | | 73/1.06 |
| 2013/0301052 A1* | 11/2013 | MacGregor | ............ | G01N 21/27 |
| | | | | 356/437 |
| 2017/0000390 A1* | 1/2017 | Biederman | ........ | A61B 5/14532 |
| 2019/0178791 A1* | 6/2019 | Stangelmayer | ........ | G01N 21/80 |
| 2019/0234920 A1* | 8/2019 | Rangel | ................... | G08B 21/12 |
| 2021/0293766 A1* | 9/2021 | Gnoerrlich | ............. | G06F 17/10 |
| 2023/0137065 A1* | 5/2023 | Takagi | .............. | G01N 33/0006 |
| | | | | 204/424 |

* cited by examiner

F I G . 1

F I G . 3
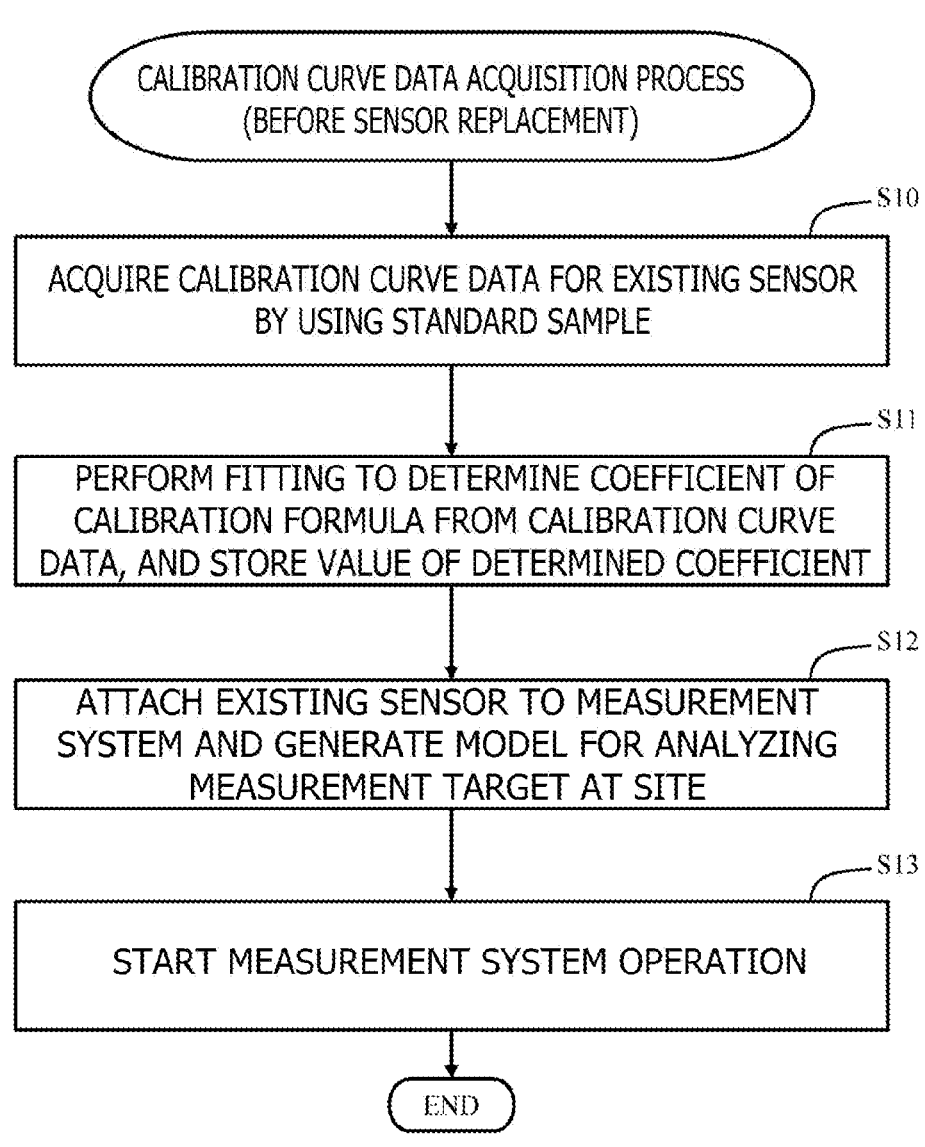

F I G . 4

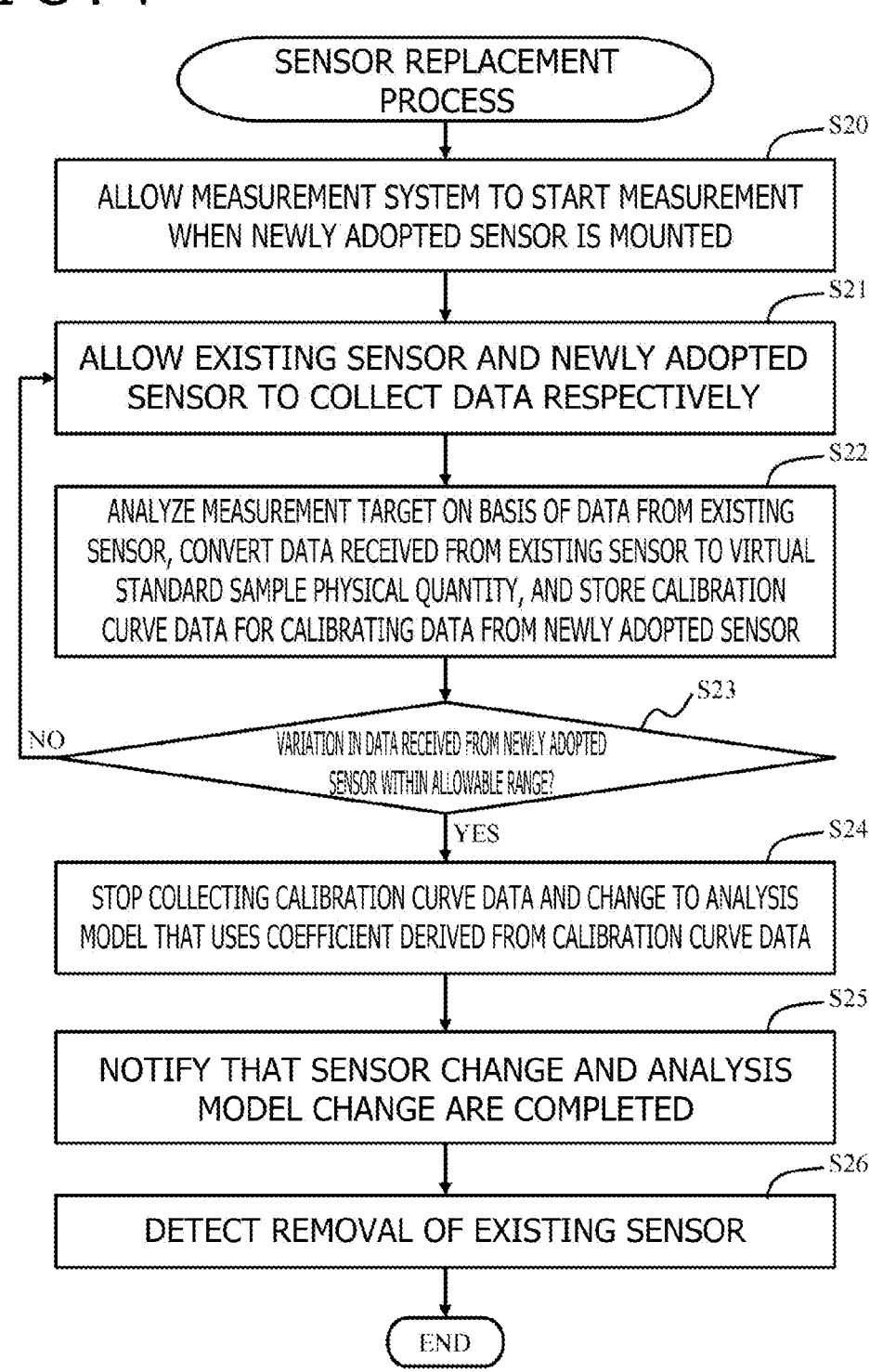

SENSOR REPLACEMENT
PROCESS

S20
ALLOW MEASUREMENT SYSTEM TO START MEASUREMENT
WHEN NEWLY ADOPTED SENSOR IS MOUNTED

S21
ALLOW EXISTING SENSOR AND NEWLY ADOPTED
SENSOR TO COLLECT DATA RESPECTIVELY

S22
ANALYZE MEASUREMENT TARGET ON BASIS OF DATA FROM EXISTING
SENSOR, CONVERT DATA RECEIVED FROM EXISTING SENSOR TO VIRTUAL
STANDARD SAMPLE PHYSICAL QUANTITY, AND STORE CALIBRATION
CURVE DATA FOR CALIBRATING DATA FROM NEWLY ADOPTED SENSOR

S23
VARIATION IN DATA RECEIVED FROM NEWLY ADOPTED
SENSOR WITHIN ALLOWABLE RANGE?

NO

YES

S24
STOP COLLECTING CALIBRATION CURVE DATA AND CHANGE TO ANALYSIS
MODEL THAT USES COEFFICIENT DERIVED FROM CALIBRATION CURVE DATA

S25
NOTIFY THAT SENSOR CHANGE AND ANALYSIS
MODEL CHANGE ARE COMPLETED

S26
DETECT REMOVAL OF EXISTING SENSOR

END

F I G . 7
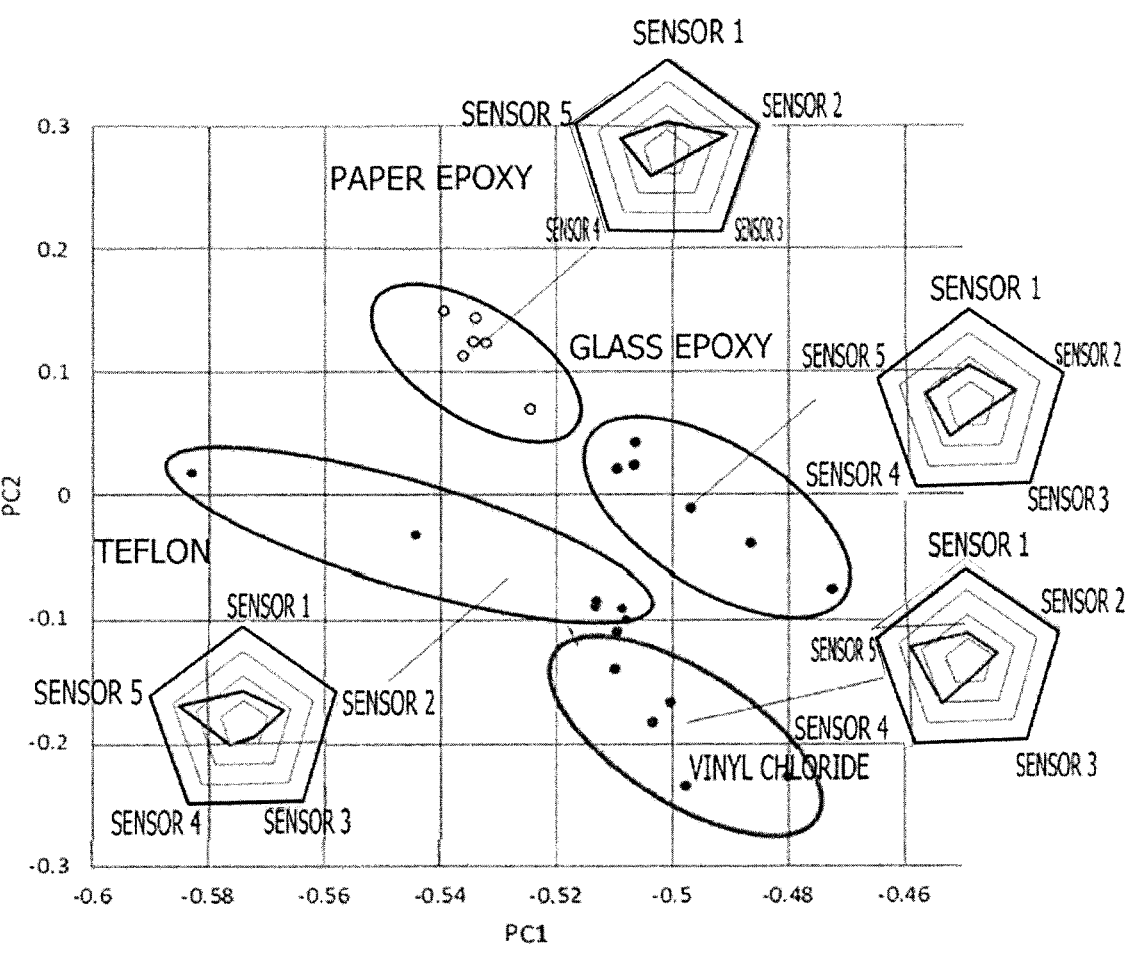

SENSOR OUTPUT VALUE

43%

● ACTUAL VALUE MEASURED BY NEWLY ADOPTED ODOR SENSOR

○ CONVERTED VALUE OF NEWLY ADOPTED ODOR SENSOR

✕ ACTUAL VALUE MEASURED BY EXISTING ODOR SENSOR CONCENTRATION

CONCENTRATION ppm

F I G . 1 2
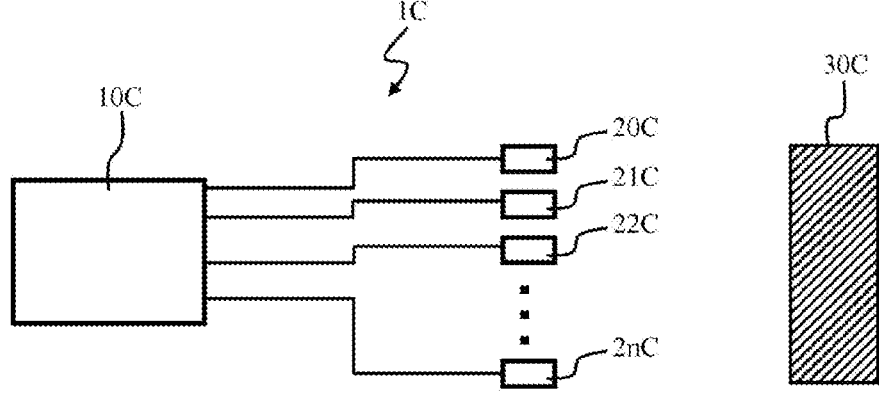
F I G . 1 3
SENSOR OUTPUT CORRESPONDING
TO PREDETERMINED PHYSICAL
QUANTITY
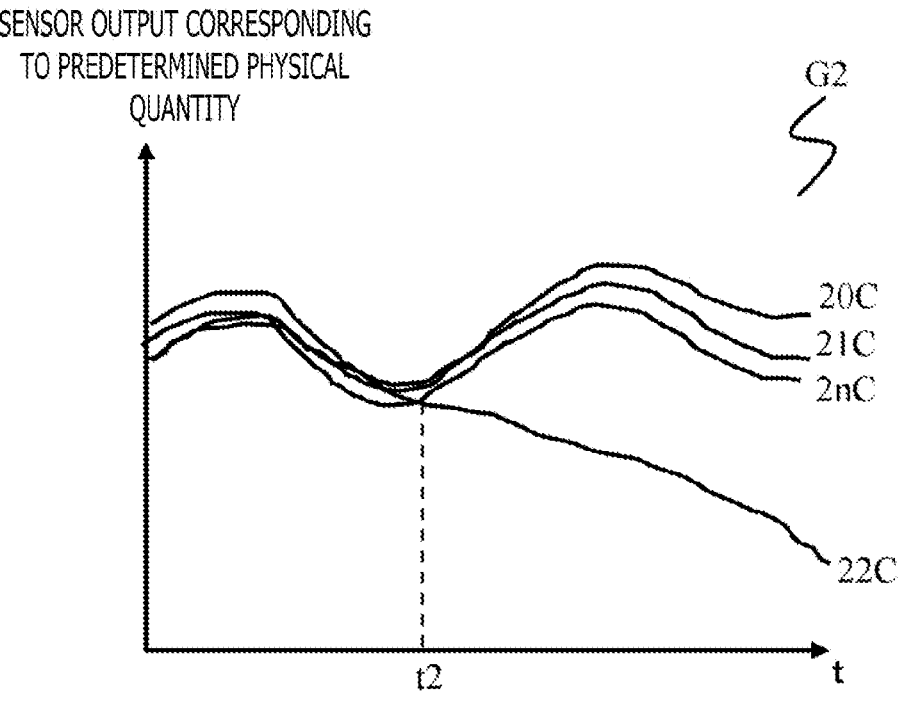

MEASUREMENT SYSTEM, MEASUREMENT METHOD, AND COMPUTER PROGRAM

BACKGROUND OF THE INVENTION

1. Field of the Invention

The present invention relates to a measurement system, a measurement method, and a computer program.

2. Description of the Related Art

There is a known measurement system for measuring a measurement target sample with a sensor to obtain measured data and grasping the on-site situation by use of an estimation model designed to analyze the measured data (JP-2008-511373-T which is referred to as Patent Document 1 hereinafter). In a case where an old sensor used by the measurement system is to be replaced with a new sensor, the new sensor needs to be calibrated in advance. Calibration data to be applied to the new sensor is often obtained by measuring a relation between a predetermined physical quantity (a standard physical quantity for acquiring calibration data) and a sensor output in an environment such as a laboratory. A technology related to a "Procedure for Calibrating a System for Continuously Measuring the Concentration of a Substance in a Bodily Fluid" is disclosed in Patent Document 1.

SUMMARY OF THE INVENTION

In a case where a new sensor is used in place of an existing old sensor, it takes time and effort to acquire data for calibrating the new sensor. Further, in a case where there is instrumental difference between characteristics of the new sensor and characteristics of the old sensor, output values of the new sensor differ from output values of the old sensor even when the same measurement target is measured. Therefore, it may become necessary to modify a machine learning model by using a sensor output value. In some cases, it may be necessary to temporarily suspend the measurement system in order to modify the machine learning model (inference model).

The present invention has been made in view of the above problems and provides an easy-to-maintain measurement system, a measurement method, and a computer program.

In order to address the above problems, according to an aspect of the present invention, there is provided a measurement system including a first sensor connected to the measurement system, a second sensor connected to the measurement system, at least one processor, and at least one memory. The first sensor measures a measurement target, and outputs a measured value of a predetermined physical quantity. The second sensor outputs the result of measurement of the measurement target, namely, a measured value of the same type as the predetermined physical quantity, and is to be newly installed for maintenance purposes. The memory stores first calibration data and an estimation model, the first calibration data relating to the first sensor and indicating a relation between the measured value and a value of the predetermined physical quantity, the estimation model being used to grasp a state of the measurement target according to the value of the predetermined physical quantity. The first calibration data indicates the value of the predetermined physical quantity that is generated by using a first measured value obtained when a known standard sample is measured by the first sensor. The processor performs (1) acquiring the first measured value from the first sensor and a second measured value from the second sensor, the first and second measured values being obtained when the measurement target is measured by the first and second sensors at a predetermined time, (2) converting the first measured value to the value of the predetermined physical quantity by use of the first calibration data, (3) calculating second calibration data for the second sensor from the second measured value and the value of the predetermined physical quantity obtained in the (2), (4) converting the second measured value to the value of the predetermined physical quantity by use of the second calibration data, and (5) detecting the state of the measurement target by use of the estimation model and the value of the predetermined physical quantity obtained in the (4).

Embodiments of the present invention make it possible to prepare for using the second sensor during the use of the first sensor and thus perform maintenance with ease.

BRIEF DESCRIPTION OF THE DRAWINGS

FIG. 1 is a diagram illustrating an overall configuration of a measurement system;

FIG. 3 is a flowchart illustrating a process of acquiring calibration data for an existing sensor;

FIG. 4 is a flowchart illustrating a sensor replacement process performed by conducting maintenance;

FIG. 7 is a diagram illustrating results obtained when a plurality of (five) sensor elements are used to measure odors emitted from burnt cables of different materials;

FIG. 12 is a diagram illustrating an overall configuration of a redundant sensing system that uses a plurality of sensors according to a fourth embodiment of the present invention;

FIG. 13 is a diagram illustrating temporal changes in output values of a plurality of sensors;

DESCRIPTION OF THE PREFERRED EMBODIMENTS

Figure 2:
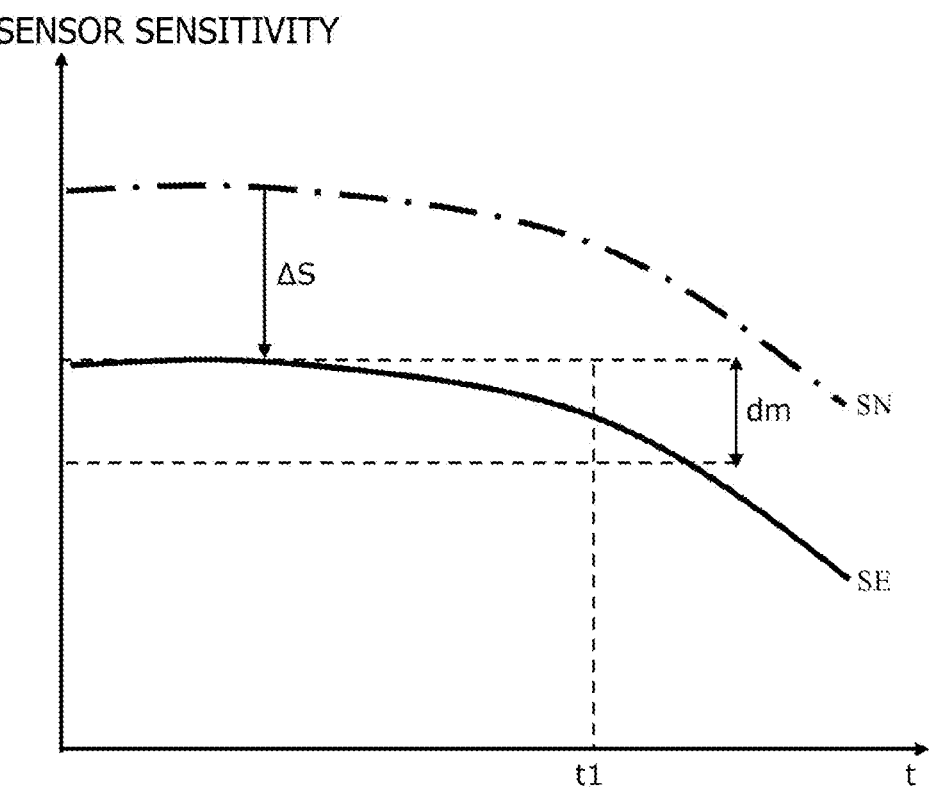
FIG. 2 is a diagram illustrating a relation between sensor performance temporal change and correction (maintenance)

Embodiments of the present invention will now be described with reference to the accompanying drawings. The embodiments disclose a measurement system that is capable of performing sensor maintenance. When maintenance such as sensor replacement or addition is to be performed, the measurement system according to the embodiments eliminates the necessity of calibrating a new sensor in a location (e.g., a laboratory or a plant) different from a site where a measurement target is present.

The measurement system according to the embodiments converts a value measured by an existing sensor to a value of a predetermined physical quantity by using first calibration data, and generates second calibration data for a newly adopted sensor from the resulting value of the predetermined physical quantity which is derived from conversion and a value measured by the newly adopted sensor. The measurement system according to the embodiments prepares for using the newly adopted sensor while continuously operating the measurement system. When the second calibration data for using the newly adopted sensor is generated, a change is made from the existing sensor to the newly adopted sensor. Subsequently, the measurement system is able to detect a state of the measurement target according to the value measured by the newly adopted sensor and a machine learning estimation model.

After a change is made from the existing sensor to the newly adopted sensor, the existing sensor may be left connected to the measurement system or disconnected from the measurement system. The existing sensor may be left as a spare sensor, and used again when the newly adopted sensor becomes abnormal or faulty. The existing sensor may be removed from the measurement system, and then the newly adopted sensor may be connected to the measurement system in place of the existing sensor. In such a case, the initial newly adopted sensor becomes a new existing sensor (and can be referred to, for example, as the second existing sensor or the previous-generation existing sensor), and a sensor newer than the initial newly adopted sensor becomes the newly adopted sensor (and can be referred to, for example, as the second new sensor or the next-generation new sensor). The measurement system can also be maintained for a long period of time while the sensors are alternately exchanged.

As described above, the embodiments eliminate the necessity of calibrating a newly adopted sensor in a location different from the measurement system. While the newly adopted sensor is connected to the measurement system and used, the measurement system generates the calibration data (second calibration data) for the newly adopted sensor, and changes from the existing sensor to the newly adopted sensor after the second calibration data is generated. Therefore, the embodiments make it possible to provide increased ease of maintenance such as sensor replacement while minimizing the downtime of the measurement system as much as possible, compared to the conventional sensor, and improve the maintainability and reliability of the measurement system. In some cases, the calibration data may be hereinafter referred to as the calibration curve data.

First Embodiment

Figure 1:
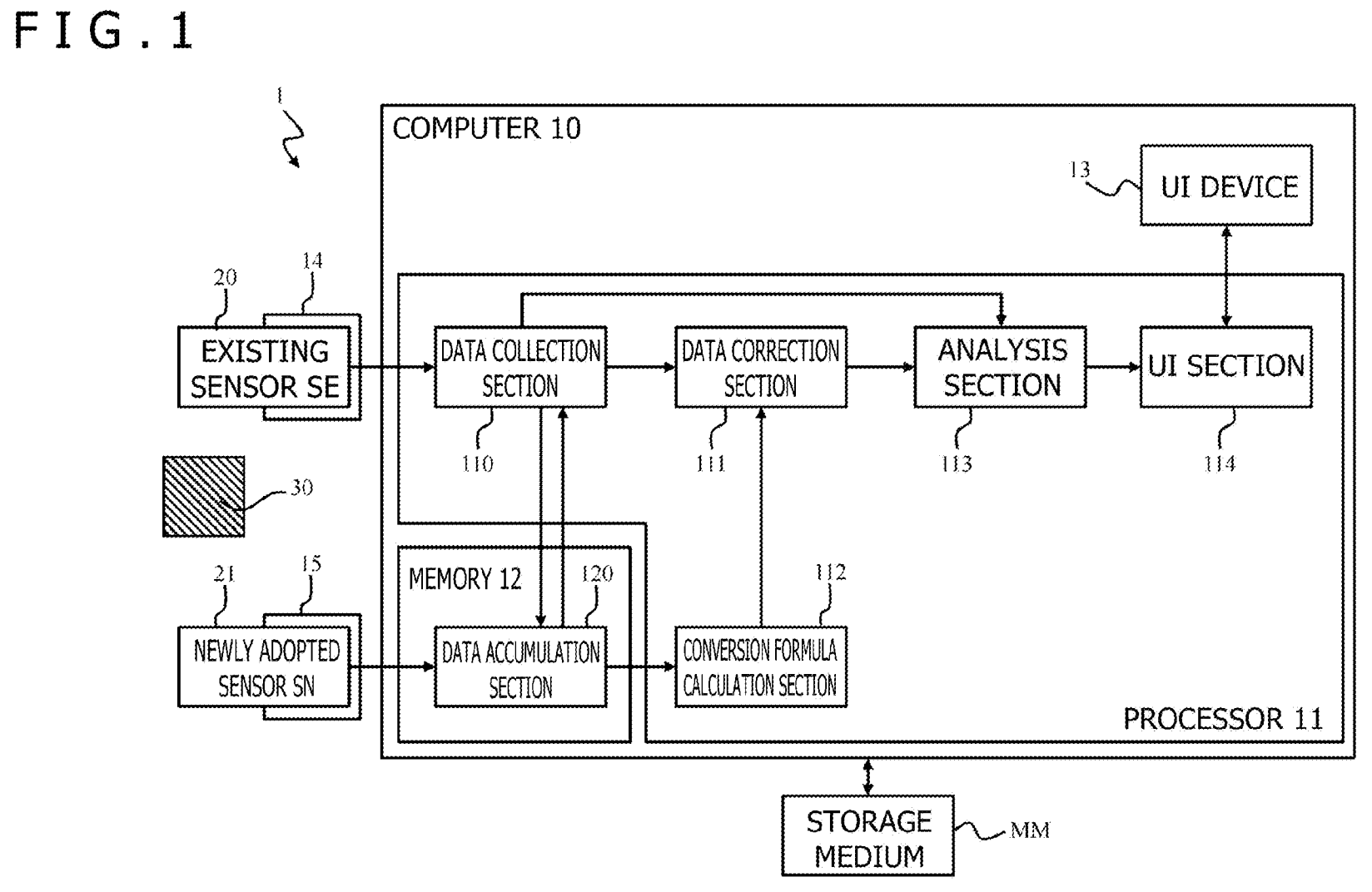

A first embodiment of the present invention will now be described with reference to FIGS. 1 to 5. The following description of the embodiment is illustrative for explaining the present invention, and omitted or simplified as needed for clarity of explanation. The present invention may be implemented in various other embodiments. Unless otherwise specified, each component element may be singular or plural.

In some cases, for ease of understanding of the present invention, for example, the position, size, shape, and range of each component element depicted in the drawings do not represent the actual position, size, shape, and range. The embodiment of the present invention is not necessarily limited, for example, to the positions, sizes, shapes, and ranges disclosed in the drawings.

In some cases, various types of information are expressed in data structures such as "table," "list," and "queue." However, the various types of information may be expressed in data structures other than the above ones. For example, the various types of information such as "XX table," "XX list," and "XX queue" may be expressed as "XX information." Expressions such as "identification information," "identifier," "name," "ID," and "number" are used to describe identification information. However, these expressions are replaceable with each other.

In some cases, a plurality of component elements having the same or similar functions are described with different suffixes added to the same reference signs. Further, in some cases where the component elements need not be distinguished from each other, such component elements are described by using their reference signs with no suffix added.

In some cases, a process performed by executing a program is described in conjunction with the embodiment. A calculating device executes a program by using a processor (e.g., a central processing unit (CPU) or a graphics processing unit (GPU)) as described later with reference to FIG. 1, and performs a process defined by the program by using, for example, storage resources and an interface device (e.g., a communication port). The storage resources include a hard disk (HD), a solid-state drive (SSD), an integrated circuit (IC) card, a secure digital (SD) card, and a digital versatile disc (DVD).

Consequently, the main constituent performing a process by executing a program may be a processor. Likewise, the main constituent performing a process by executing a program may be a controller, an apparatus, a system, a calculating device, or a node having a processor. The main constituent performing a process by executing a program may be a computing unit and may include a dedicated circuit configured to perform a specific process. Here, the dedicated circuit is, for example, a field-programmable gate array (FPGA), an application-specific integrated circuit (ASIC), a complex programmable logic device (CPLD), or the like.

The program may be installed on the calculating device from a program source. The program source may be, for example, a program distribution server or a computer-readable storage medium. In a case where a program distribution server is used as the program source, the program distribution server may include a processor and storage resources that store a program for distribution, and the processor included in the program distribution server may distribute the program for distribution to other calculating devices. Further, in the embodiment, two or more programs may be implemented as one program, and one program may be implemented as two or more programs.

FIG. 1 illustrates a configuration of a measurement system 1. As illustrated in FIG. 1, the measurement system 1 includes, for example, a computer 10 and a plurality of (two) sensors 20 or 21.

The sensor 20 is an existing sensor that is already in use, and corresponds to a "first sensor." The sensor 21 is a new sensor (a newly adopted sensor) that is to be used in place of the existing sensor, and corresponds to a "second sensor." The sensors 20 and 21 are electrically connected to the computer 10 in a wired or wireless manner. The existing sensor 20 is electrically connected to the computer 10 through a first sensor mount 14. The newly adopted sensor 21 is electrically connected to the computer 10 through a second sensor mount 15. The sensors 20 and 21 are detachably mounted on the first and second sensor mounts 14 and 15. The first and second sensor mounts 14 and 15 are examples of "sensor slots."

The computer 10 includes, for example, a processor 11 and a memory 12. The computer 10 may include a user interface device 13 (the term "user interface" is abbreviated to UI in the drawings). Further, the computer 10 may additionally include, for example, an undepicted communication circuit, an undepicted input/output circuit, and the like.

The memory 12 is a storage device that includes a main storage device and an auxiliary storage device. The memory 12 may use storage elements of any type. The memory 12 includes a data accumulation section 120 that has a function of accumulating data collected by a data collection section 110.

The processor 11 is a circuit that performs computing processing. The processor 11 is, for example, a CPU, a GPU, or a combination of these units. The processor 11 is not limited to a CPU or a GPU. Any semiconductor device configured to perform a predetermined process may be used as the processor 11.

The processor 11 includes, for example, the data collection section 110, a data correction section 111, a conversion formula calculation section 112, an analysis section 113, and a user interface section 114. In other words, by executing a predetermined computer program stored in the memory 12, the processor 11 implements a process 110 of collecting data, a process 111 of correcting data, a process 112 of calculating a conversion formula, a process 113 of analyzing a state of a measurement target 30, and a process 114 of inputting and outputting data to and from the user interface device 13.

The data collection section 110 has a function of collecting sensor output values from the sensors 20 and 21 (the sensor output values may be referred to also as the output values or the measured values). The conversion formula calculation section 112 has a function of calculating a conversion formula for converting an acquired sensor output value to the value of a predetermined physical quantity. The conversion formula is a formula for converting a sensor output value of the newly adopted sensor 21 to the value of a predetermined physical quantity, and corresponds to an example of the "second calibration data."

The data correction section 111 has a function of correcting the sensor output values according to the conversion formula sent from the conversion formula calculation section 112. The analysis section 113 has a function of receiving the results of measurements made by the sensors from the data correction section 111, and analyzing the state of the measurement target 30. The user interface section 114 has a function of receiving the result of analysis made by the analysis section 113, and providing information to a user of the measurement system 1 through the user interface device 13. The user is also able to change at least some setting values used by the measurement system 1 through the user interface section 114 by using the user interface device 13.

The user interface device 13 includes an information providing device (not depicted) and an information input device (not depicted). The information proving device provides information to the user. The information input device receives information inputted by the user. The information providing device is, for example, a monitor display, a printer, a voice synthesis device, a lamp, or the like. The information input device is, for example, a keyboard switch, a touch panel, a voice instruction device, or the like. An alternative is to use a combination of the information providing device and the information input device, such as a head-mounted display.

A storage medium MM is connected to the computer 10 in a wired or wireless manner, and used to input and output the computer program and/or data which is hereinafter referred to as the computer program and/or the like to and from the computer 10. The storage medium MM stores the computer program and/or the like in a non-transitory manner. The storage medium MM is, for example, a flash memory device, a hard disk, a magnetic tape, a magnetic disk, or an optical disk. Another computer (not depicted) connected to the computer 10 through a communication network can be used as the storage medium MM. That is, the computer program and/or the like can also be installed on the computer 10, for example, from a server or a storage system connected to the communication network.

The sensors 20 and 21 are described below. The sensors 20 and 21 are sensors of basically the same model or sensors of substantially the same model. The sensors 20 and 21 are, for example, odor sensing sensors or object length measurement sensors as described later.

The existing sensor 20 is a sensor targeted for replacement. The existing sensor 20 can also be referred to as the first sensor 20 or the old sensor 20. The newly adopted sensor 21 is a new sensor that is to be used in place of the existing sensor 20. The newly adopted sensor 21 can also be referred to as the second sensor 21 or the new sensor 21.

These two sensors 20 and 21 are able to simultaneously measure the measurement target 30. The sensor output values of these two sensors 20 and 21 are transmitted to the computer 10. The measurement system 1 is able to concurrently use these two sensors 20 and 21, namely, the old and new sensors. However, the existing sensor 20 is used to detect the state of the measurement target 30. When the newly adopted sensor 21 becomes ready for use such that change is made from the existing sensor 20 to the newly adopted sensor 21, the state of the measurement target 30 is detected according to the sensor output value from the newly adopted sensor 21.

The measurement target 30 is a target object that is to be measured by the measurement system 1 to determine the value of a predetermined physical quantity. The predetermined physical quantity is information indicating a physical property of an object, and is, for example, concentration, length, pressure, temperature, voltage, current, or resistance. A psychophysical quantity derived, for example, from the sense of sight, taste, touch, or smell may be regarded as equivalent to a physical quantity and included in the predetermined physical quantity. The psychophysical quantity is, for example, odor, color, or illuminance.

The measurement target 30 may be in a solid, liquid, or gaseous state. A location where the measurement system 1 detects (grasps) the state of the measurement target 30 is hereinafter referred to as the site.

The state before the replacement of the existing sensor 20 is described below. Before being used by the measurement system 1 to grasp the state of the measurement target 30, standard sample calibration data for converting the output value of the sensor 20 to the predetermined physical quantity is stored in the data accumulation section 120. The standard sample calibration data is, for example, the data acquired for converting the output value to distance when the sensor 20 is a length measurement sensor or to concentration when the sensor 20 is a gas sensor.

The output value which is acquired by the sensor 20 is sent to the data collection section 110. The data collection section 110 references the standard sample calibration data stored in the data accumulation section 120, and converts the output value of the sensor 20 to a predetermined physical quantity. The value obtained by conversion is sent from the data collection section 110 to the data correction section 111.

In a case where the data of the sensor need not be corrected as described later, the predetermined physical quantity obtained by the data collection section 110 is sent to the analysis section 113 without being corrected by the data correction section 111. The analysis section 113 analyzes the state of the measurement target 30. For example, a machine learning (ML) model is included in the analysis section 113. Based on the predetermined physical quantity, the analysis section 113 estimates or analyzes to grasp the state of the measurement target 30 that the user wants to know.

An estimation model for use in the analysis section 113 can be, for example, the aforementioned machine learning model, a model derived from a physical theoretical formula, or a mathematical model for principal component analysis, clustering analysis, or the like.

Information indicating the state of the measurement target 30 which is estimated or analyzed by the analysis section 113 is sent to the user interface section 114, and provided from the user interface section 114 to the user through the user interface device 13. By viewing the information displayed on the user interface device 13, the user is able to know the state of the measurement target 30. The state of the measurement target 30 may be, for example, information regarding the value of the predetermined physical quantity, information regarding a change in the value of the predetermined physical quantity, or information (failure probability or an estimated replacement interval) derived from statistical processing of the value of the predetermined physical quantity.

Further, in a case, for example, where the measurement system 1 measures the distance to the measurement target 30, the measurement system 1 is able to issue an alarm if the measured distance is above or below an allowable range. The measurement system 1 is also able to measure the concentration of a gas in the measurement target 30, determine whether or not food regarded as the measurement target 30 is normal, and output the result of determination on the basis of the result of measurement.

A procedure for replacing the sensor 20 is described below with reference to FIG. 2. In FIG. 2, the sensitivity of the existing sensor 20 is indicated by the sign SE, and the sensitivity of the newly adopted sensor 21 is indicated by the sign SN. It is assumed that the sensitivity of the existing sensor 20 decreases with time. If the sensitivity of the existing sensor 20 decreases with time below a preset design margin dm, the sensor output value is converted to the value of a predetermined physical quantity with decreased accuracy. More specifically, if the sensitivity of the sensor 20 decreases with time, the output value of the sensor 20 is converted with decreased accuracy to the predetermined physical quantity through the use of the standard sample calibration data (first calibration data).

In order to maintain the reliability of the measurement system 1, the replacement of the existing sensor 20 with an entirely new sensor 21 at a recommended replacement interval t1 (e.g., two years) is considered before a predetermined performance value (sensitivity in the case depicted in FIG. 2) of the existing sensor 20 deviates from the design margin dm. When the predetermined performance value of the existing sensor 20 falls within the design margin dm, the measurement system 1 calculates the recommended replacement interval t1. The recommended replacement interval t1 may be calculated, for example, on the basis of the inventory or delivery of the newly adopted sensor 21. The recommended replacement interval t1 may be calculated on the basis of an interval (predicted value) at which the predetermined performance value of the existing sensor 20 deviates from the design margin dm and the procurement (inventory, delivery, etc.) of the newly adopted sensor 21.

In the usual case, the newly adopted sensor 21 and the existing sensor 20 are of the same model. However, even when the sensors 20 and 21 are of the same model, there may exist a difference ΔS in performance (sensitivity in the present and subsequent cases) between the existing sensor 20 and the newly adopted sensor 21 due to instrumental difference. In a case where the design margin dm assumed by the measurement system 1 is exceeded by the performance difference ΔS as depicted in FIG. 2, measurement accuracy decreases. Therefore, it is necessary to correct the output value of the newly adopted sensor 21.

In the present embodiment, the output value of the newly adopted sensor 21 is corrected in a manner described below. As described with reference to FIG. 1, the newly adopted sensor 21 and the existing sensor 20 are both connected to the computer 10, and the newly adopted sensor 21 senses the measurement target 30 at the same time as the existing sensor 20. The output value of the existing sensor 20 and the output value of the newly adopted sensor 21 are sent to the data collection section 110.

The method of data correction will be described in detail later. However, the flow of processing for correcting the data of the newly adopted sensor 21 is as described below. The output values (measured values) of the two sensors 20 are 21 which have measured the same measurement target 30 as depicted in FIG. 1 are delivered to the conversion formula calculation section 112 through the data accumulation section 120. By using the standard sample calibration data obtained in advance, the conversion formula calculation section 112 converts the data of the existing sensor 20 in need of replacement to a predetermined physical quantity (e.g., distance when the sensor 20 is a length measurement sensor or concentration when the sensor 20 is a gas sensor). The calibration data regarding the newly adopted sensor 21 can be formed on the basis of the relation between the resulting physical quantity and the output value of the newly adopted sensor 21. The calibration data which is newly formed is used to create a conversion formula or table for converting the output value of the newly adopted sensor 21 to the output value of the existing sensor 20. The data correction section 111 converts the output value of the sensor 21 to the output value of the sensor 20 by using the created conversion formula or table. The value obtained by conversion is sent to the analysis section 113. The analysis section 113 estimates the state of the measurement target 30 by using the data converted to the output value of the sensor 20. Since the output value of the newly adopted sensor 21 is converted to the output value of the existing sensor 20 and inputted to the analysis section 113, the analysis section 113 is able to make analysis with data measured by the newly adopted sensor 21 without changing, for example, analysis parameters of a machine learning model.

The present embodiment configured as described above provides the following operational advantages.
1) Formerly, in a case where the performance curve of a sensor, that is, the calibration curve of the sensor as depicted in FIG. 2, varies due to instrumental difference or the like, the calibration curve for the newly adopted sensor 21 needs to be additionally obtained before replacement by using a standard sample having a known physical quantity, as is the case with the existing sensor 20. However, the present embodiment eliminates the necessity of acquiring the calibration data before the newly adopted sensor 21 is connected to the measurement system 1.

2) Since the output value (measured value) of the newly adopted sensor 21 is converted to the output value (measured value) of the existing sensor 20 which has been used thus far, it is not necessary to change the parameters of an analysis model that is employed by the analysis section 113. Usually, after the existing sensor 20 is replaced with the newly adopted sensor 21, it is necessary to acquire training data for machine learning at a measurement site where the measurement system 1 is used, and then perform a model update. However, the present embodiment eliminates the necessity of performing such a model update.

3) The present embodiment uses the two sensors 20 and 21 to measure the same measurement target 30, converts the output value of the existing sensor 20 to a predetermined physical quantity, and acquires the calibration data for the newly adopted sensor 21. It is expectable that the present embodiment will provide higher accuracy than a method of directly comparing the output values of the two sensors 20 and 21 to determine the correlation between them and directly converting the output value of the newly adopted sensor 21 to the output value of the existing sensor 20 according to the determined correlation. This will be described later.

The flowchart of FIG. 3 illustrates a calibration data acquisition procedure that is performed by the measurement system 1 according to the present embodiment before sensor replacement. FIGS. 1 and 2 will be referenced as needed.

First of all, the measurement system 1 prepares for measuring the measurement target 30 (step S10). The existing sensor 20 is used to measure a standard sample having a known physical quantity (e.g., a standard sample having a known distance in the case of a length measurement sensor or having a known concentration in the case of a gas sensor). The calibration curve data (first calibration data) for the existing sensor 20 is acquired from the result of measurement (step S10).

The coefficient of a calibration formula for converting to the physical quantity of the standard sample is determined from the calibration curve data by using a mathematical method such as fitting, and the determined coefficient is stored in the data accumulation section 120 (step S11).

The existing sensor 20 is installed at a site. A model for grasping the state of the measurement target 30 (e.g., an estimation model, an analysis model, or a machine learning model; hereinafter referred to as the analysis model) is built on the basis of the result of measurement of the measurement target 30 by the existing sensor 20. The model built in this manner is stored in the analysis section 113 (step S12).

After completion of steps S10 to S12 above, the measurement system 1 starts measurement operation at the site (step S13).

A sensor replacement procedure will now be described with reference to the flowchart of FIG. 4. When it is determined that the existing sensor 20 is in need of replacement, the process depicted in FIG. 4 starts. The necessity for sensor replacement may be determined on the basis of a graph depicted in FIG. 2, or the like by the administrator or the user of the measurement system 1 or determined by the measurement system 1 itself.

The newly adopted sensor 21 is installed at the site where the measurement target 30 is present, and connected to the computer 10 of the measurement system 1 to start measurement (step S20).

The measurement system 1 causes the sensors 20 and 21 to measure the same measurement target 30 and transmit measurement result data (output values) to the data collection section 110 (step S21).

The analysis section 113 inputs the data of the existing sensor 20 to the analysis model, estimates or analyzes the state of the measurement target 30, converts the data of the existing sensor 20 to a virtual standard sample concentration, and accumulates the calibration curve data for the newly adopted sensor 21 (step S22).

The measurement system 1 determines whether variation in the calibration curve data for the newly adopted sensor 21 obtained in step S22 is within an allowable range (step S23).

Figure 5:
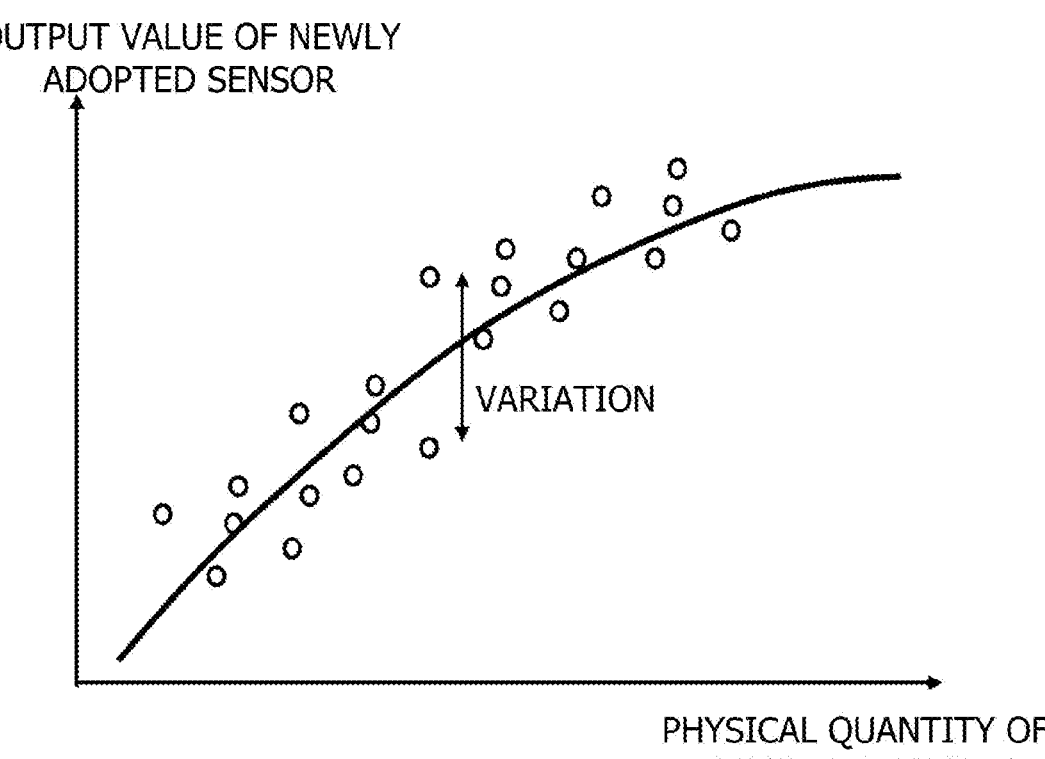
FIG. 5 is a diagram illustrating a calibration curve that is used to calibrate a new sensor (second sensor)

The variation in the calibration curve data is described below with reference to FIG. 5. The vertical axis in FIG. 5 represents the output value of the newly adopted sensor 21. The horizontal axis in FIG. 5 represents the physical quantity of the standard sample used to acquire the calibration curve data for the existing sensor 20. The variation indicates the extent to which the obtained data varies from the calibration curve determined by fitting. If the variation is not within a predetermined allowable range ("NO" at step S23), the measurement system 1 returns to step S21 and continues to make measurements by using the existing sensor 20 and the newly adopted sensor 21. If the variation falls within the predetermined allowable range ("YES" at step S23), the measurement system 1 proceeds to step S24.

When the variation falls within the allowable range, the measurement system 1 terminates calibration curve data collection (step S21) for the newly adopted sensor 21, and changes to an analysis model that uses the coefficient derived from the calibration curve for the newly adopted sensor 21 (step S24). In step S24, after the conversion formula for the output value of the newly adopted sensor 21 is determined in the conversion formula calculation section 112 and the data of the newly adopted sensor 21 is corrected in the data correction section 111, the estimation model of the analysis section 113 is changed to a model that uses the coefficient derived from the acquired calibration curve for the newly adopted sensor 21.

The measurement system 1 notifies the administrator (or the user; hereinafter the same applies) of the measurement system 1 of the completion of model modification processing and sensor change processing from the user interface section 114 through the user interface device 13 (step S25).

Subsequently, the existing sensor 20 is disconnected from the computer 10 and removed from the measurement system 1. The administrator is notified of the removal of the existing sensor 20 from the measurement system 1 through the user interface section 114 and the user interface device 13 (step S26). Subsequently, a newer sensor may be attached to the first sensor mount 14 from which the existing sensor 20 has been removed.

As described with reference to the flowchart of FIG. 4, the calibration data need not be newly acquired for the newly adopted sensor 21 before it is attached to the measurement system 1. The measurement system 1 is able to acquire the calibration data for the newly adopted sensor 21 while using both the new and old sensors 20 and 21, and thus reduce the amount of processing for changing from the existing sensor 20 to the newly adopted sensor 21. Further, as described in step S22 of FIG. 4, the calibration data for using the newly adopted sensor 21 is created while analyzing the state of the measurement target 30 by using the output value of the existing sensor 20. Therefore, the downtime of the measurement system 1 due to sensor replacement can be shortened. The present embodiment having the above-described configuration makes it possible to easily perform maintenance on the measurement system 1 and efficiently keep the reliability of the measurement system 1.

Second Embodiment

A second embodiment of the present invention will now be described with reference to FIGS. 6 to 10. The second embodiment deals with a case where the measurement system 1 according to the first embodiment is applied to an odor measurement system 1A. The second and subsequent embodiments will be described mainly with respect to the difference from the first embodiment.

Figure 6:
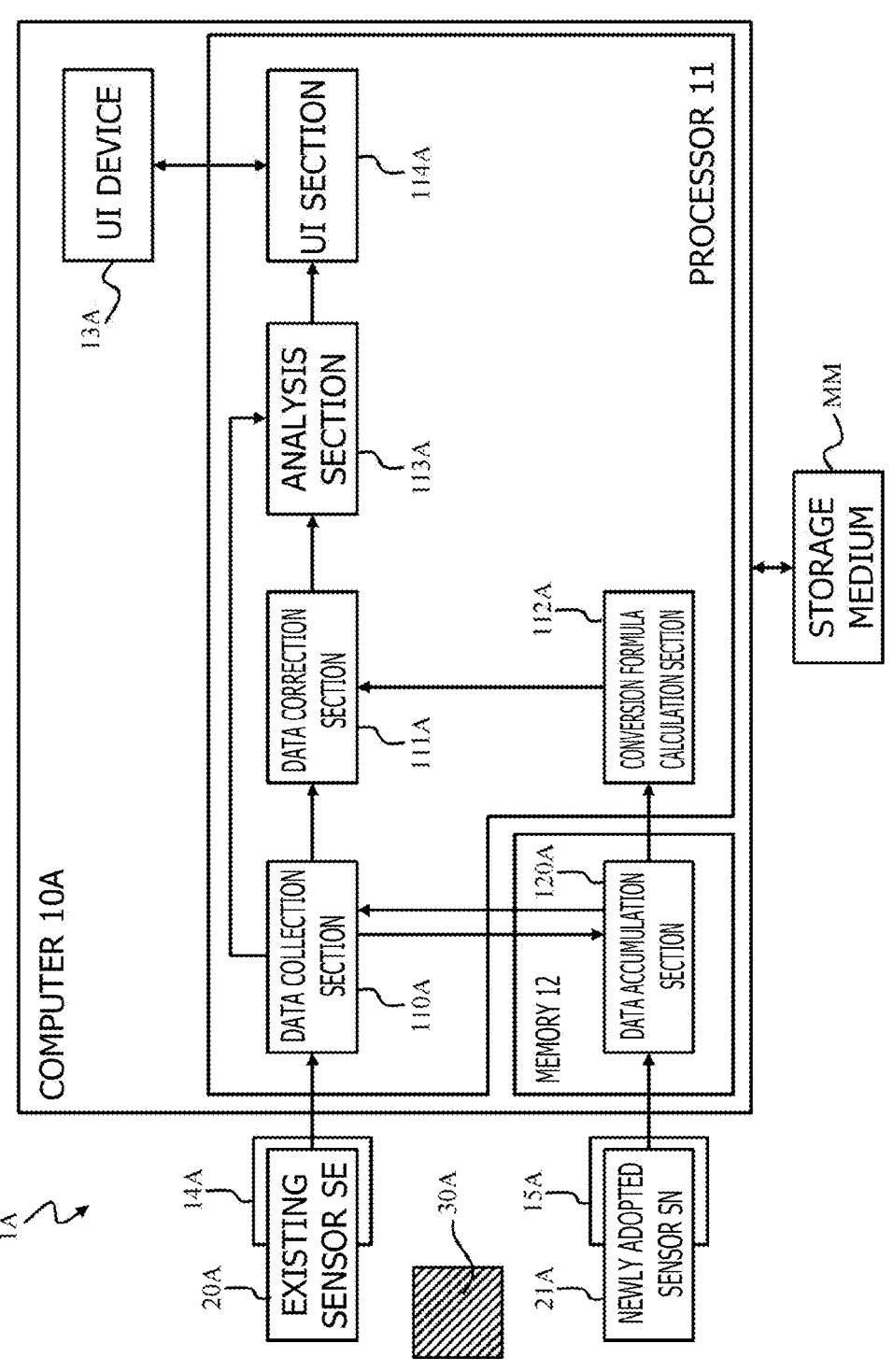
FIG. 6 is a diagram illustrating an overall configuration of a system that measures odors according to a second embodiment of the present invention.
Figure 8:
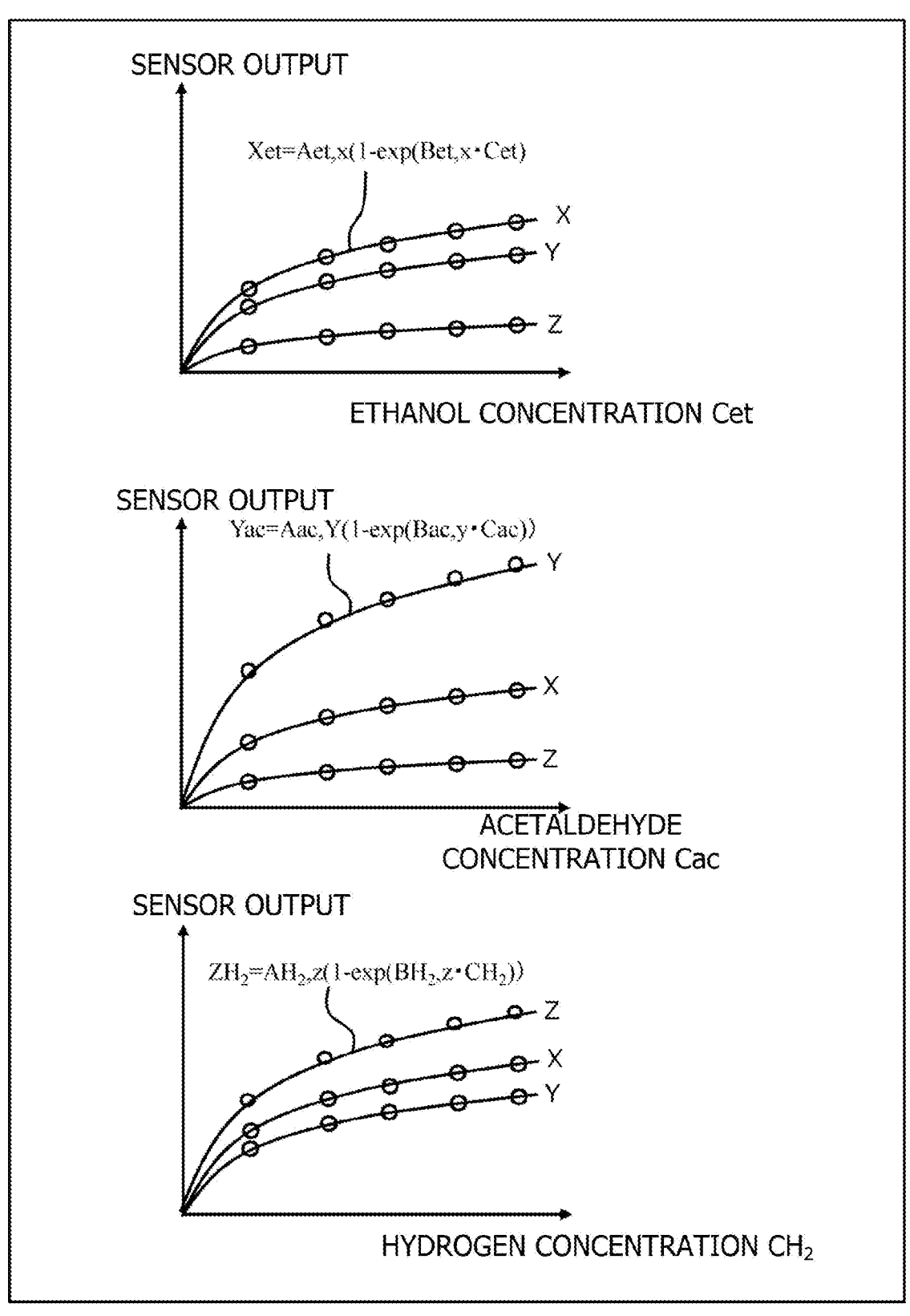
FIG. 8 is a diagram illustrating a calibration curve for an odor sensor.
Figure 9:
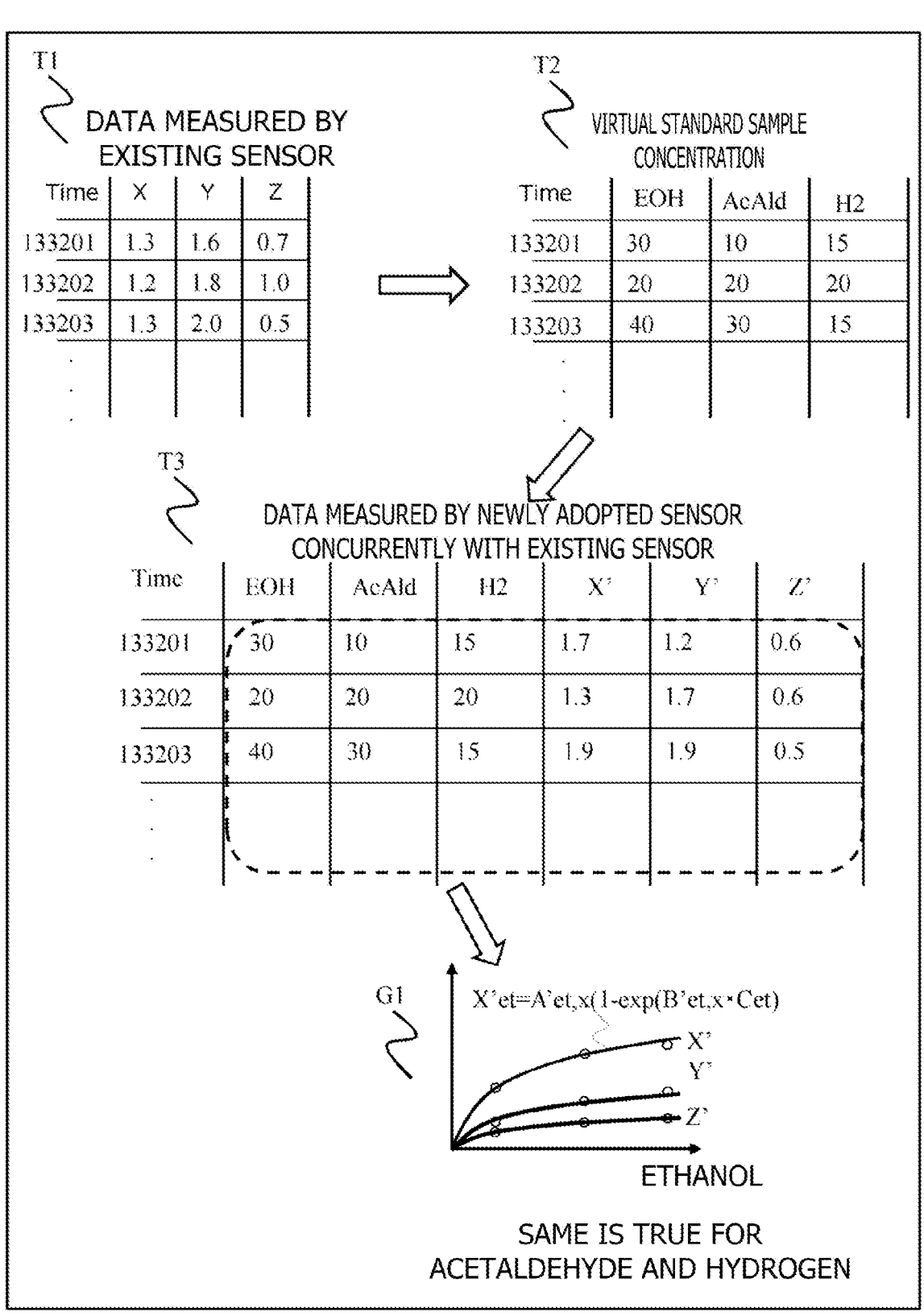
FIG. 9 is an explanatory diagram illustrating how to acquire calibration curves for a new odor sensor.
Figure 10:
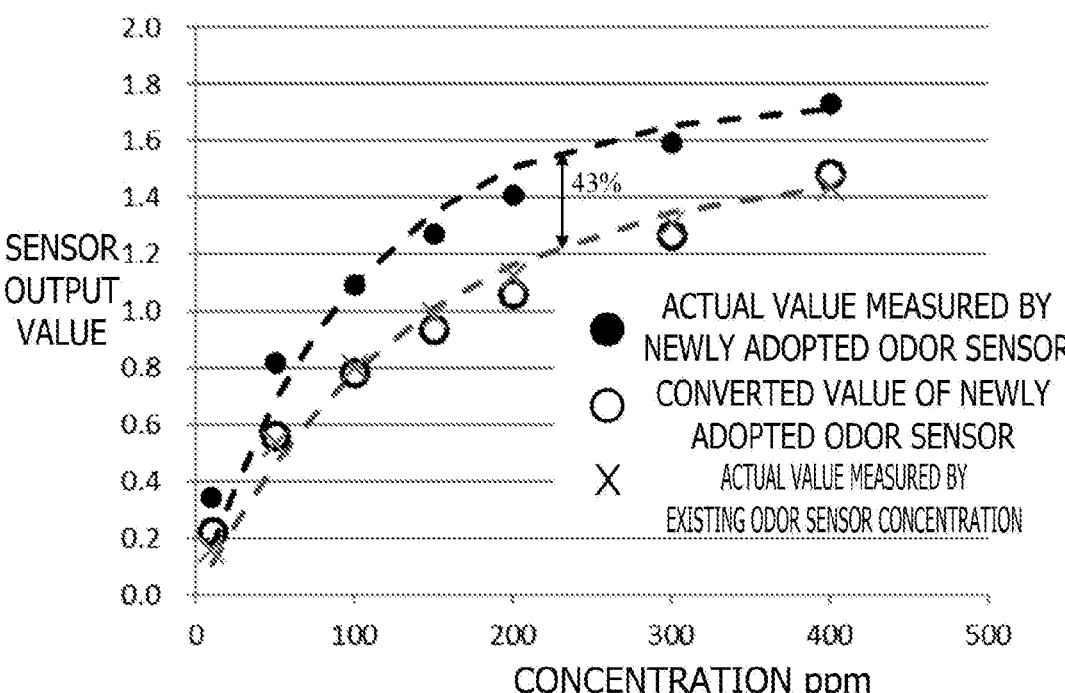
FIG. 10 is a diagram illustrating advantages that are provided by converting sensor output values.

FIG. 6 is a diagram illustrating an overall configuration of the odor measurement system 1A. FIG. 7 is a diagram illustrating the results obtained when a plurality of (five) sensor elements are used to measure odors emitted from burnt cables of different materials. FIG. 8 is a diagram illustrating a calibration curve for an odor sensor. FIG. 9 is an explanatory diagram illustrating how to acquire the calibration curve for a newly adopted odor sensor. FIG. 10 is a diagram illustrating advantages that are provided by converting sensor output values.

A configuration of the odor measurement system 1A is described below with reference to FIG. 6. As is the case with the measurement system 1 depicted in FIG. 1, the odor measurement system 1A includes an existing odor sensor 20A which corresponds to the "first sensor," a newly adopted odor sensor 21A which corresponds to the "second sensor," and a computer 10A.

The odor sensors 20A and 21A are electrically connected to the computer 10A in a wired or wireless manner. The existing odor sensor 20A is electrically connected to the computer 10A through a first sensor mount 14A. The newly adopted odor sensor 21A is electrically connected to the computer 10A through a second sensor mount 15A. The odor sensors 20A and 21A are detachably mounted on the first and second sensor mounts 14A and 15A.

The computer 10A includes, for example, a processor 11 and a memory 12. The computer 10A can also include a user interface device 13A (the term "user interface" is abbreviated to UI in the drawings). Further, the computer 10A may additionally include an undepicted communication circuit, an undepicted input/output circuit, and the like.

The memory 12 is a storage device that includes a main storage device and an auxiliary storage device. The memory 12 may use storage elements of any type. The memory 12 includes a data accumulation section 120A that has a function of accumulating data collected by a data collection section 110A.

The processor 11 is a circuit that performs computing processing. The processor 11 includes, for example, a data collection section 110A, a data correction section 111A, a conversion formula calculation section 112A, an analysis section 113A, and a user interface section 114A. In other words, by executing a predetermined computer program stored in the memory 12, the processor 11 implements a process 110A of collecting data, a process 111A of correcting data, a process 112A of calculating a conversion formula, a process 113A of analyzing the state of a measurement target 30A, and a process 114A of inputting and outputting data to and from the user interface device 13A.

The data collection section 110A has a function of collecting sensor output values from the odor sensors 20A and 21A. The conversion formula calculation section 112A has a function of calculating a conversion formula for converting an acquired sensor output value to the value of a predetermined physical quantity. The data correction section 111A has a function of correcting the sensor output values according to the conversion formula sent from the conversion formula calculation section 112A. The analysis section 113A has a function of receiving the results of measurements made by the odor sensors from the data correction section 111A, and analyzing the state of the measurement target 30A. The user interface section 114A has a function of receiving the result of analysis made by the analysis section 113A, and providing information to a user of the odor measurement system 1A through the user interface device 13A. The user is also able to change at least some setting values used by the odor measurement system 1A from the user interface device 13A through the user interface section 114A.

The odor sensors 20A and 21A each include a gas sensor chip of a semiconductor type or of an electrochemical type, and the sensor output values (e.g., voltage values) vary with the components or concentration of a target gas. The gas sensor chip is an example of a "sensor element." A plurality of (e.g., five) sensor chips are disclosed in FIG. 7.

The odor sensor 20A is an existing sensor in need of replacement. The odor sensor 21A is a newly adopted sensor that is to be used in place of the existing odor sensor 20A. The two odor sensors 20A and 21A can be concurrently used to measure the measurement target 30A. The output values of the two odor sensors 20A and 21A are transmitted to the computer 10A.

The odor sensors 20A and 21A are described in detail below. The odor sensor 20A includes a plurality of sensor chips having different properties in order to distinguish between various odors. The individual sensor chips generate different output values according to the difference between odor components to be measured. Therefore, when the odor components of the measurement target 30A differ from each other, the individual sensor chips generate different output values. By using such properties of the sensor chips, it is possible to detect different odors of the measurement target 30A.

FIG. 7 illustrates the results obtained when odor sensors including five different types of sensor chips having different properties are used to measure odors emitted from burnt cables of different materials.

As mentioned above, the output values of the five sensor chips differ from each other due to the different odor components. FIG. 7 illustrates the results obtained when the output values of the five sensors are subjected to principal component analysis and classified. The vertical and horizontal axes in FIG. 7 are two principal component axes of measured data.

The vertices of a pentagon graph respectively correspond to the five types of sensor chips. When viewed clockwise, the vertices respectively correspond to a first sensor chip (sensor 1 in FIG. 7), a second sensor chip (sensor 2 in FIG. 7), a third sensor chip (sensor 3 in FIG. 7), a fourth sensor chip (sensor 4 in FIG. 7), and a fifth sensor chip (sensor 5 in FIG. 7). The pentagon graph includes four similar pentagons. The smallest pentagon is "0.1," the second smallest pentagon is "0.3," the third smallest pentagon is "0.5," and the largest pentagon positioned outermost is "0.7."

The position in the graph varies from one cable material to another. Further, odors emitted from burnt cables of the same material are grouped in positions close to each other. Therefore, the above-described analysis method makes it possible to identify the type of a burnt cable. More specifically, the odor components can be estimated by analyzing, with a machine learning model, the output values of the individual sensor chips and the measured data of the different odor components.

Returning to FIG. 6, the data collection section 110A stores the standard sample calibration data for converting the output value of the existing odor sensor 20A to the gas concentration of a predetermined component. The output value obtained by the existing odor sensor 20A is sent to the data collection section 110A.

In a case where the sensor output values need not be corrected, the measured sensor output values of the individual sensor chips are sent to the analysis section 113A without being corrected by the data correction section 111A. In the analysis section 113A, as mentioned above, for example, a machine learning mode is used to estimate or analyze what odor is emitted. In a case indicated by the above example, the analysis section 113A estimates or analyzes an unusual burning smell and the type of a burnt material.

The state of the measurement target 30 estimated or analyzed by the analysis section 113A is sent to the user interface section 114A, and the measurement target 30 is subjected to information processing and data processing required by the user. The result of such processing is provided to the user through the user interface device 13A.

For example, in a case where an abnormal odor, that is, an unusual burning smell, is sensed in a factory where various odors exist under normal conditions, the odor measurement system 1A notifies the user, the administrator, factory workers, and the like that the abnormal odor is sensed. Meanwhile, in a case where the odor measurement system 1A makes measurements in a food factory, the odor measurement system 1A is able to estimate, for example, whether food preparation or processing is normally conducted and whether food is unspoiled, and provide the results of estimation to the user through the user interface device 13.

The following describes how the odor measurement system 1A converts the data of the output value of the newly adopted odor sensor 21A in a case where the existing odor sensor 20A needs to be replaced.

FIG. 8 illustrates how the output values of three sensor chips X, Y, and Z, which are included in the existing odor sensor 20A, change according to the type and concentration of each gas. These three sensor chips respectively have properties exhibiting relatively high sensitivity to three gases, namely, ethanol, acetaldehyde, and hydrogen. Graphs in FIG. 8 depict calibration curves, that is, information regarding changes that occur in the sensor output values of the sensor chips X, Y, and Z when the concentrations of the three gases, namely, ethanol, acetaldehyde, and hydrogen, are changed. The upper graph in FIG. 8 indicates a case where ethanol is measured. The middle graph in FIG. 8 indicates a case where acetaldehyde is measured. The lower graph in FIG. 8 indicates a case where hydrogen is measured.

The data of the above-mentioned calibration curves is collected before the odor measurement system 1A starts measurement operation at an actual measurement site. That is, the data of each calibration curve is collected in step S10 of FIG. 3.

Points indicated by circles within each graph in FIG. 8 are obtained by changing each component concentration C represented by the horizontal axis and plotting the output values of the sensor chips X, Y, and Z. The formula indicated in each graph of FIG. 8 is a calibration curve formula that expresses the relation between the sensor output values X, Y, and Z of each sensor and the corresponding component concentrations C. Coefficients A and B of such a calibration curve formula can be determined, for example, from the points indicated by the circles through the use of the least-squares method.

After the odor sensor 20A is installed at a site such as a factory, various odors are machine-learned to build a model. When the model is built, the odor measurement system 1A starts operation. When the sensitivity of the odor sensor 20A decreases with time, whether or not to replace the odor sensor 20A is determined. This determination may be made by the user including the administrator or may be automatically made by the odor measurement system 1A. The odor measurement system 1A is able to provide information supporting the determination of the replacement interval to the user from the user interface device 13A.

A procedure for replacing a deteriorated sensor 20A (existing odor sensor) is described below with reference to FIG. 4 as appropriate.

First of all, the newly adopted odor sensor 21A is installed at a state where the measurement target 30A is present, and used to measure odors. The output values of the three sensor chips X, Y, and Z included in the existing odor sensor 20A and the output values of three sensor chips X', Y', and Z' included in the newly adopted odor sensor 21A are sent to the data collection section 110A. The output values of the three sensor chips X, Y, and Z of the existing odor sensor 20A are delivered to the analysis section 113A and inputted to an analysis model for estimating the state of odor of the measurement target 30A (at the site). This causes the analysis section 113A to estimate the state of the measurement target 30A.

Simultaneously with the above-described regular analysis process, the output values of the sensor chips X, Y, and Z of the existing odor sensor 20A are converted to virtual standard sample concentrations as indicated in tables T1 and T2 of FIG. 9. As the standard sample components to be used in this instance, the components (ethanol, acetaldehyde, and hydrogen) used at the time of acquisition of the above-described calibration curve data are selected.

As indicated in table T3 of FIG. 9, the obtained virtual standard sample concentrations are linked with the output values of the three sensor chips X', Y', and Z' of the newly adopted odor sensor 21A, which simultaneously makes measurements. As indicated by a graph G1 in FIG. 9, the above linking operation results in the accumulation of data equivalent to the calibration curve related to the sensor chips X', Y', and Z'. The formula for data of the employed points may use an instantaneous value or an average value over a predetermined time period. Determination may be made as needed depending on the use case.

As the number of points indicated by the circles plotted in the graph of FIG. 9 increases with time, the accuracy of the calibration curve increases. In a case where a predetermined threshold is exceeded by the accuracy of the calibration curve data (in a case where the query in step S23 of FIG. 4 is answered "YES"), the variation of data from the newly adopted odor sensor 21A is within the allowable range, and the accuracy of the newly adopted odor sensor 21A is determined to be sufficiently high. This concludes a process of acquiring the calibration curve data for the newly adopted odor sensor 21A.

Values of parameters A' and B' of the calibration curve formula for the three chip sensors X', Y', and Z' are determined from the acquired calibration curve data. The processes of determining the values of parameters A' and B' are performed in the conversion formula calculation section 112A. The calibration curve formula and the parameters for each of the old and new sensors 20A and 21A are sent to the data correction section 111A.

The output values of the newly adopted odor sensor 21A which are sent to the data collection section 110A are corrected by the data correction section 111A to the output values equivalent to the output values of the existing odor sensor 20A. More specifically, on the basis of the relation between the acquired calibration curves for the two sensors (old and new sensors), the data correction section 111A converts the output value of the newly adopted odor sensor 21A to an output value equivalent to the output value of the existing odor sensor 20A.

Subsequently, the analysis section 113A and the user interface section 114A perform processing in a similar manner to the situation where the existing odor sensor 20A is not changed yet.

The above description deals with a case where three sensor chips are used. However, similar procedures are also applicable to a case where the number of included sensor chips is two or less or four or more.

FIG. 10 is a diagram illustrating advantages provided by the present embodiment. Black circles indicate an actual measured value (measured value; hereinafter the same applies) of the newly adopted odor sensor 21A. White circles indicate a value derived from conversion of the actual measured value of the newly adopted odor sensor 21A to the measured value of the existing odor sensor 20A. Crosses indicate the actual measured value of the existing odor sensor 20A.

The average difference between the calibration curve for the newly adopted odor sensor 21A (the curve formed by joining the black circles) and the calibration curve for the existing odor sensor 20A (the curve formed by joining the crosses) is approximately 43%. Meanwhile, the average difference between the calibration curve for the existing odor sensor 20A and the calibration curve obtained by converting the actual measured value of the newly adopted odor sensor 21A to the measured value of the existing odor sensor 20A (the curve formed by joining the white circles) is approximately 5%.

That is, the second embodiment provides the same operational advantages as the first embodiment. The odor measurement system 1A according to the second embodiment is able to collect data necessary for calibrating the newly adopted odor sensor 21A while using the existing odor sensor 20A, and use the measured value of the newly adopted odor sensor 21A in the same way as for the measured value of the existing odor sensor 20A.

Third Embodiment

Figure 11:
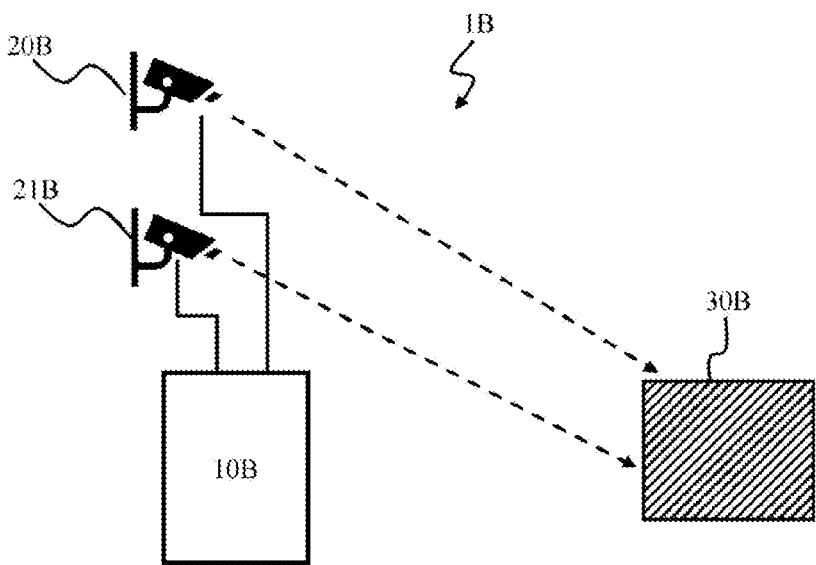
FIG. 11 is a diagram illustrating an overall configuration of a system that measures a length of an object according to a third embodiment of the present invention.

A third embodiment of the present invention will now be described with reference to FIG. 11. The third embodiment will be described on the assumption that a length measurement system 1B is used as the measurement system. FIG. 11 is a diagram illustrating an overall configuration of the length measurement system 1B according to the third embodiment. As is the case with the measurement system depicted in FIG. 1, the length measurement system 1B includes length measurement sensors 20B and 21B and a computer 10B. The existing length measurement sensor 20B and the newly adopted length measurement sensor 21B are connected to the computer 10B in a wired or wireless manner. The internal configuration of the computer 10B is similar to the internal configuration depicted in FIG. 1 and will not be described in detail.

The length measurement sensors 20B and 21B measures lengths by optical principles, for example, through the use of a time-of-flight (ToF) sensor. However, any length measurement principles may be used. The length measurement system 1B is used, for example, to determine the position of a workpiece in a factory or grasp the position of an object moving in a room.

The following describes a case where the currently used length measurement sensor 20B is deteriorated over time and in need of replacement. Whether the existing length measurement sensor 20B should be replaced may be determined by the user of the length measurement system 1B according to a change in the measured value of the existing length measurement sensor 20B or may be automatically determined and reported to the user by the length measurement system 1B.

Even when the newly adopted length measurement sensor 21B and the existing length measurement sensor 20B are of the same model and have the same performance characteristics such as measurement resolution, the measured value (output value; hereinafter the same applies) of the newly adopted length measurement sensor 21B slightly differs from the measured value of the existing length measurement sensor 20B in a case where the same measurement target 30B is measured. The slight difference between the measured values of the length measurement sensors 20B and 21B is due to instrumental difference caused, for example, by the difference between the temperatures of the length measurement sensors 20B and 21B or the difference in external light affecting the length measurement sensors 20B and 21B. In some other cases, the length measurement sensors 20B and 21B are mounted at slightly different angles or positions, so that the position or distance of the measurement target 30B which is derived from the output values of the two sensors 20B and 21B differs between the two sensors 20B and 21B. In a case where the existing length measurement sensor 20B is to be replaced with the newly adopted length measurement sensor 21B, the newly adopted length measurement sensor 21B is generally calibrated before it is installed at a measurement site.

In contrast, in the present embodiment, the newly adopted length measurement sensor 21B is installed in the length measurement system 1B, connected to the computer 10B, and allowed to measure the measurement target 30B concurrently with the existing length measurement sensor 20B. Subsequently, in the present embodiment, the measured value of the existing length measurement sensor 20B is converted to a predetermined physical quantity by using the calibration data acquired in advance for the existing length measurement sensor 20B, and then the physical quantity derived from conversion is used to acquire the calibration data for the newly adopted length measurement sensor 21B. This enables the length measurement system 1B according to the present embodiment to convert the output value of the newly adopted length measurement sensor 21B to a value equivalent to the output value of the existing length measurement sensor 20B. The present embodiment configured as described above also provides the same operational advantages as the first embodiment.

Fourth Embodiment

A fourth embodiment of the present invention will now be described with reference to FIGS. 12 and 13. A measurement system 1C according to the fourth embodiment is a redundant sensing system that constantly measures one measurement target 30C with a plurality of sensors 20C to 2nC. In the example described below, it is assumed that three sensors are used to measure the measurement target 30C. Alternatively, however, measurements may be constantly made by using two sensors or four or more sensors.

In order to be able to constantly measure the same measurement target 30C with two or more sensors, the measurement system 1C includes two or more sensor slots (sensor mounts). The output values of the sensors detachably mounted in the sensor slots are almost simultaneously inputted to the data collection section in a computer 10C for measurement purposes. Therefore, the measurement system 1C is able to compare the output values of the sensors to determine whether the performance of the sensors is degraded over time.

FIG. 12 illustrates an overall configuration of the measurement system 1C according to the present embodiment. As described above, the measurement system 1C includes the sensors 20C to 2nC and the computer 10C. The sensors 20C to 2nC are connected to the computer 10C in a wired or wireless manner. The internal configuration of the computer 10C is similar to the internal configuration depicted in FIG. 1 and will not be redundantly described. The sensors 20C to 2nC may be gas sensors (odor sensors) or length measurement sensors.

As depicted in FIG. 12, the sensors 20C to 2nC are of the same model and configured to measure the same measurement target 30C. The output values measured by the sensors 20C to 2nC are converted to a predetermined physical quantity of the standard sample in a manner similar to the one described in conjunction with the foregoing embodiments.

A graph G2 in FIG. 13 indicates how the predetermined physical quantity acquired by the sensors 20C to 2nC varies with time.

The measurement target 30C itself varies with time. Therefore, the output values of the sensors 20C to 2nC also vary in response to the variation of the measurement target 30C. However, the values derived from conversion to the predetermined physical quantity are approximately close to each other.

As indicated by the graph G2, after a time t2, only the value of the predetermined physical quantity derived from the conversion of the output value of a certain sensor 22C is deviated by a predetermined quantity or more from the values of the predetermined physical quantity derived from the other sensors 20C to 2nC. This signifies that the performance of the sensor 22C is degraded, and implies that the sensor 22C is in need of replacement (see FIG. 2). A common method for extracting a sensor whose performance is degraded is to check for deviation from an average value of the values of the predetermined physical quantity of sensors other than a target sensor. However, a different mathematical method may alternatively be used. The present embodiment configured as described above also provides the same operational advantages as the first embodiment.

Fifth Embodiment

Figure 14:
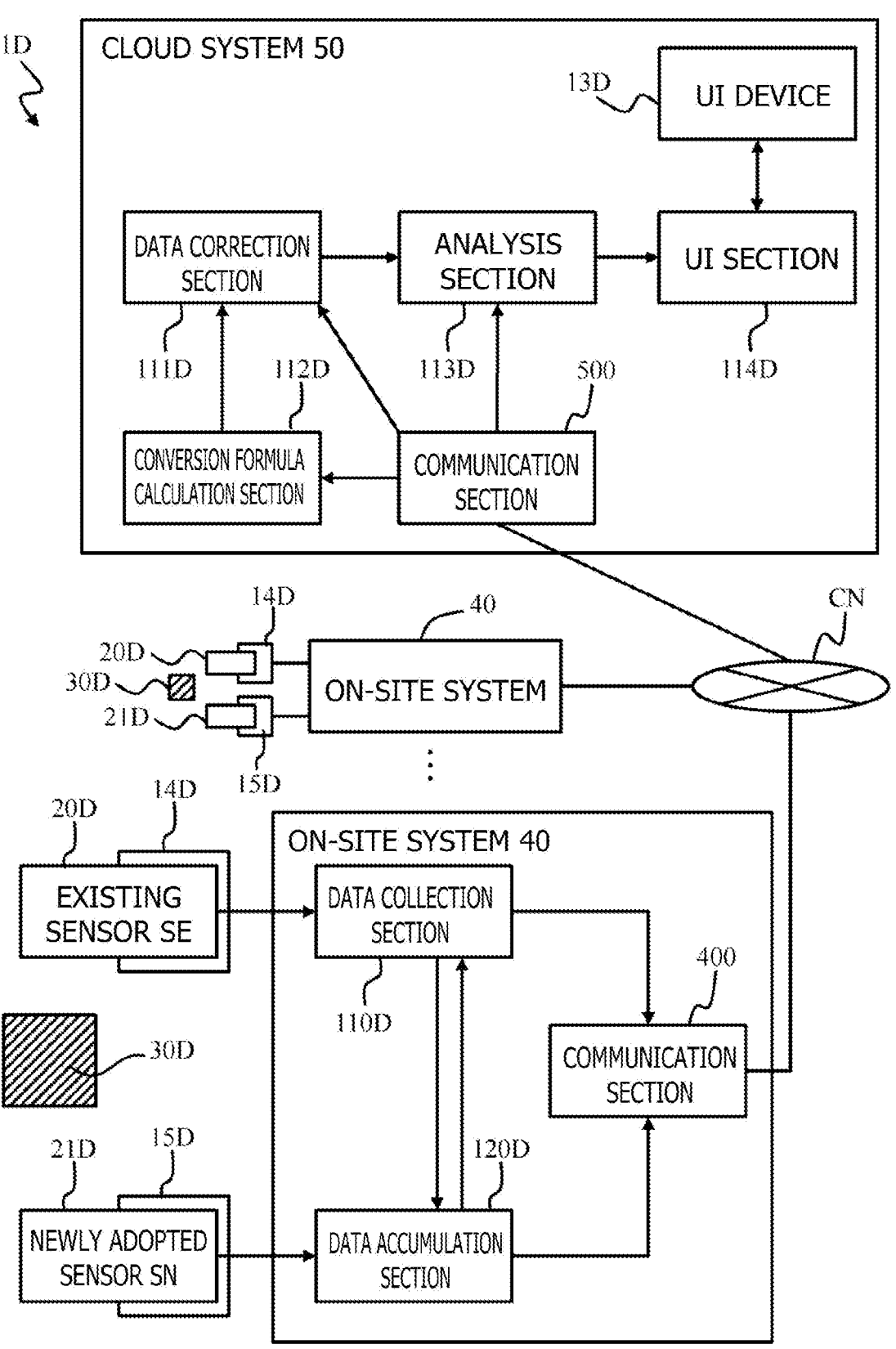
FIG. 14 is a diagram illustrating an overall configuration of the measurement system according to a fifth embodiment of the present invention.

A fifth embodiment of the present invention will now be described with reference to FIG. 14. FIG. 14 is a diagram illustrating an overall configuration of a measurement system 1D according to the fifth embodiment. The measurement system 1D according to the present embodiment includes an on-site system 40 and a cloud system 50. The on-site system 40 is disposed at a measurement site. The cloud system 50 is connected to at least one on-site system 40 through a communication network CN.

The on-site system 40 is an information processing apparatus that is installed at a measurement site where a measurement target 30D is present. The on-site system 40 includes, for example, a data collection section 110D, a data accumulation section 120D, and a communication section 400. The on-site system 40 is provided with a plurality of sensor mounts 14D and 15D. Sensors 20D and 21D are detachably mounted on the sensor mounts 14D and 15D. The on-site system 40 transmits the output values of the sensors 20D and 21D to the cloud system 50 from the communication section 400 through the communication network CN on a periodic or nonperiodic basis.

The cloud system 50 is a computer that is connected to at least one on-site system 40. The cloud system 50 includes, for example, a communication section 500, a conversion formula calculation section 112D, a data correction section 111D, an analysis section 113D, a user interface section 114D, and a user interface device 13D. Functions 110D, 111D, 112D, 113D, 114D, and 120D which are implemented by the above-mentioned sections are similar to earlier-described functions 110, 111, 112, 113, 114, and 120, and will not be redundantly described.

The measurement system 1D according to the present embodiment configured as described above enables the cloud system 50 to process and analyze sensor output values transmitted from a plurality of on-site systems that are respectively installed at a plurality of measurement sites. The present embodiment configured as described above also provides the same operational advantages as the first embodiment.

Sixth Embodiment

A sixth embodiment of the present invention will now be described with reference to FIG. 15. According to an instruction from a production management system 60, a measurement system 1E according to the sixth embodiment starts a process of changing from an existing sensor 20E to a newly adopted sensor 21E.

The production management system 60 is a system that manages production at a site where a measurement target 30E is present, and is an example of a "host system." The "host system" is not limited to the production management system 60, and may alternatively be another system such as a maintenance management system.

Figure 15:
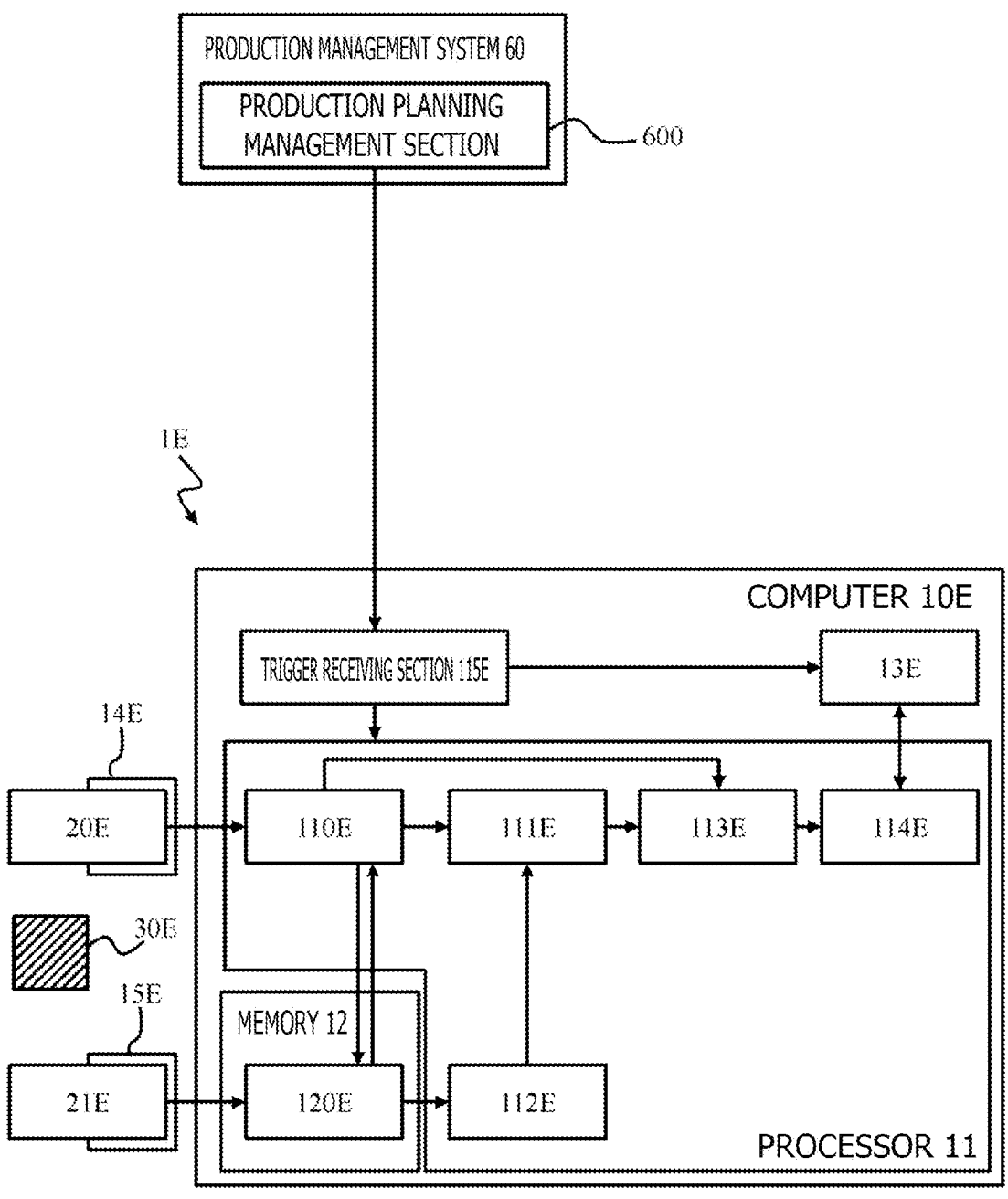
FIG. 15 is a diagram illustrating an overall configuration of the measurement system according to a sixth embodiment of the present invention.

FIG. 15 is a diagram illustrating an overall configuration of the measurement system 1E according to the present embodiment. The measurement system 1E includes a plurality of sensors 20E and 21E and a computer 10E. The sensors 20E and 21E are detachably mounted on sensor mounts 14E and 15E.

Functions 110E, 111E, 112E, 113E, 114E, and 120E which are incorporated in the computer 10E are similar to the earlier-described functions 110, 111, 112, 113, 114, and 120, and will not be redundantly described.

The computer 10E further includes a trigger receiving section 115E. Upon receipt of a sensor change instruction from a production planning management section 600 in the production management system 60, the trigger receiving section 115E starts a sensor change process (transition process) of changing from the existing sensor 20E to the newly adopted sensor 21E, for example, by simultaneously using the sensors 20E and 21E and creating the calibration data for the newly adopted sensor 21E in a manner described in conjunction with the first embodiment and the like.

The present embodiment configured as described above also provides the same operational advantages as the first embodiment. Further, the present embodiment starts the sensor change process according to an instruction from the production management system 60 which is the host system. This makes it possible to change from the existing sensor 20E to the newly adopted sensor 21E at a time appropriate for a sensor change. For example, in a case where a measuring or monitoring process is performed with the existing sensor 20E only under predetermined conditions, the production management system 60 is also able to issue the sensor change instruction to the measurement system 1E at a time when the predetermined conditions are met.

It should be noted that the present invention is not limited to the foregoing embodiments. A person skilled in the art will appreciate that, for example, various additions, modifications, and the like may be made without departing from the scope of the present invention. The foregoing embodiments are not limited to example configurations depicted in the accompanying drawings. The configurations and processing methods adopted by the foregoing embodiments may be changed as appropriate within the scope of achieving the objective of the present invention.

Further, the component elements to be included in the embodiments of the present invention may be selected as appropriate. The present invention also extends to embodiments that are configured to include such appropriately selected component elements. Furthermore, the component elements described in the appended claims can be used in combinations other than the combinations explicitly stated in the appended claims. Some component elements of an embodiment can be replaced by the component elements of another embodiment, and the component elements of an embodiment can be added to the component elements of another embodiment. Moreover, some component elements of each embodiment can be subjected to the addition of other component elements, deleted, or replaced by other component elements.

Control lines and information lines considered necessary for explanation are depicted in conjunction with the foregoing embodiments, and all the control lines and information lines required for products are not necessarily depicted. Actually, it may be regarded that almost all component elements are interconnected. Further, the foregoing embodiments can be used in combination as appropriate.

What is claimed is:

1. A measurement system comprising:
a first sensor connected to the measurement system;
a second sensor connected to the measurement system;
at least one processor; and
at least one memory,
wherein the first sensor measures a measurement target, and outputs a measured value of a predetermined physical quantity,
the second sensor outputs the result of measurement of the measurement target, namely, a measured value of same type as the predetermined physical quantity, and is to be newly installed for maintenance purposes,
the memory stores first calibration data and an estimation model, the first calibration data relating to the first sensor and indicating a relation between the measured value and a value of the predetermined physical quantity, the estimation model being used to grasp a state of the measurement target according to the value of the predetermined physical quantity, the first calibration data indicates the value of the predetermined physical quantity that is generated by using a first measured value obtained when a known standard sample is measured by the first sensor, and
the processor is configured to perform steps of
(1) acquiring the first measured value from the first sensor and a second measured value from the second sensor, the first and second measured values being obtained when the measurement target is measured by the first and second sensors at a predetermined time,
wherein, the predetermined physical quantity represents a concentration of each of a plurality of types of gas, and
the first sensor and the second sensor are odor sensors that respectively include a plurality of sensor elements configured to output independent measured values;
(2) converting the first measured value to the value of the predetermined physical quantity by use of the first calibration data,
(3) calculating second calibration data for the second sensor from the second measured value and the value of the predetermined physical quantity obtained in step (2),
(4) converting the second measured value to the value of the predetermined physical quantity by use of the second calibration data, and
(5) detecting the state of the measurement target by use of the estimation model and the value of the predetermined physical quantity obtained in step (4), and
(6) disconnecting the first senor from the measurement system upon completion of step (5).

2. The measurement system according to claim 1, wherein the measured value and the value of the predetermined physical quantity that are indicated by the first calibration data and the second calibration data are in a nonlinear relation, and step (4) includes a convergence calculation for converting a plurality of the measured values to a plurality of the values of the predetermined physical quantity.

3. The measurement system according to claim 1,
wherein the predetermined physical quantity indicates a distance to the measurement target or a position of the measurement target, and
the first sensor and the second sensor measure the measurement target.

4. The measurement system according to claim 1, further comprising:
a first sensor slot having the first sensor provided therein; and
a second sensor slot having the second sensor provided therein.

5. The measurement system according to claim 1, further comprising:
a user interface device that is connected to the processor,
wherein the processor has a function of causing the user interface device to output information regarding the detected state of the measurement target.

6. The measurement system according to he measurement system according to wherein the predetermined time is a same sampling interval that is applied to the first sensor and the second sensor.

7. The measurement system according to claim 1, wherein steps (1) to (4) are performed when designated by a host system.

8. The measurement system according to claim 1,
wherein, at a time when the first sensor is in need of replacement, the measurement system is connected to the second sensor to perform steps (1) to (4).

9. The measurement system according to claim 1, wherein the measurement system is connected to a plurality of sensors that measure the measurement target and output the measure values of the predetermined physical quantity, and the first sensor is selected as a replacement target from among the plurality of sensors according to change of the measured values outputted from the plurality of sensors with time.

10. A measurement method using a measurement system that includes a first sensor connected to the measurement system, a second sensor connected to the measurement system, at least one processor, and at least one memory, the first sensor measuring a measurement target and outputting a measured value of a predetermined physical quantity, the second sensor outputting a result of measurement of the measurement target, namely, a measured value of same type as the predetermined physical quantity and being to be newly installed for maintenance purposes, the measurement method comprising:

causing the memory to store first calibration data and an estimation model, the first calibration data relating to the first sensor and indicating a relation between the measured value and a value of the predetermined physical quantity, the estimation model being used to grasp a state of the measurement target according to the value of the predetermined physical quantity, the first calibration data indicating the value of the predetermined physical quantity that is generated by using a first measured value obtained when a known standard sample is measured by the first sensor; and causing the processor to perform steps comprising (1) acquiring the first measured value from the first sensor and a second measured value from the second sensor, the first and second measured values being obtained when the measurement target is measured by the first and second sensors at a predetermined time, wherein, the predetermined physical quantity represents a concentration of each of a plurality of types of gas, and the first sensor and the second sensor are odor sensors that respectively include a plurality of sensor elements configured to output independent measured values;

(2) converting the first measured value to the value of the predetermined physical quantity by use of the first calibration data, (3) calculating second calibration data for the second sensor from the second measured value and the value of the predetermined physical quantity obtained in step (2), (4) converting the second measured value to the value of the predetermined physical quantity by use of the second calibration data, and (5) detecting the state of the measurement target by use of the estimation model and the value of the predetermined physical quantity obtained in step (4), and (6) disconnecting the first sensor from the measurement system upon completion of step (5).

11. The measurement method according to claim 10, wherein steps (1) to (4) are implemented when the processor executes a predetermined computer program stored in the memory.

12. The measurement method according to claim 11, wherein, at a time of calculation of the second calibration data described in steps (3) and (4), acquisition of the second calibration data in step (3) is determined by setting an allowable range of variation of the second measured value with respect to a relational expression for converting the second measured value to the value of the predetermined physical quantity and confirming that the variation of the second measured value is within the allowable range.

13. A non-transitory computer-readable medium upon which is embodied instructions which, when executed by a processor, cause the processor to perform a measurement method using a measurement system that includes a first sensor connected to the measurement system, a second sensor connected to the measurement system, at least one processor, and at least one memory, the first sensor measuring a measurement target and outputting a measured value of a predetermined physical quantity, the second sensor outputting a result of measurement of the measurement target, namely, a measured value of same type as the predetermined physical quantity and being to be newly installed for maintenance purposes, the measurement method comprising:

storing first calibration data and an estimation model, the first calibration data relating to the first sensor and indicating a relation between the measured value and a value of the predetermined physical quantity, the estimation model being used to grasp a state of the measurement target according to the value of the predetermined physical quantity, the first calibration data indicating the value of the predetermined physical quantity that is generated by using a first measured value obtained when a known standard sample is measured by the first sensor;

acquiring the first measured value from the first sensor and a second measured value from the second sensor, the first and second measured values being obtained when the measurement target is measured by the first and second sensors at a predetermined time, wherein, the predetermined physical quantity represents a concentration of each of a plurality of types of gas, and the first sensor and the second sensor are odor sensors that respectively include a plurality of sensor elements configured to output independent measured values;

converting the first measured value to the value of the predetermined physical quantity by use of the first calibration data;

calculating second calibration data for the second sensor from the second measured value and the value of the predetermined physical quantity obtained in said step of converting the first measured value;

converting the second measured value to the value of the predetermined physical quantity by use of the second calibration data; and detecting the state of the measurement target by use of the estimation model and the value of the predetermined physical quantity obtained in said step of converting the second measured value, and disconnecting the first senor from the measurement system upon completion of the detecting the state of the measurement target.

* * * * *